US009492410B2

(12) United States Patent
Fariello et al.

(10) Patent No.: US 9,492,410 B2
(45) Date of Patent: *Nov. 15, 2016

(54) METHODS FOR TREATMENT OF PARKINSON'S DISEASE

(71) Applicant: Newron Pharmaceuticals, S.P.A., Bresso (MI) (IT)

(72) Inventors: Ruggero Fariello, Luino (IT); Carlo Cattaneo, Milan (IT); Patricia Salvati, Arese (IT); Luca Benatti, S. Maurizio al Lambro (IT)

(73) Assignee: NEWRON PHARMACEUTICALS S.P.A., Bresso (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/532,925

(22) Filed: Nov. 4, 2014

(65) Prior Publication Data

US 2015/0150833 A1 Jun. 4, 2015

Related U.S. Application Data

(60) Continuation of application No. 13/594,621, filed on Aug. 24, 2012, now Pat. No. 8,901,176, which is a division of application No. 10/559,982, filed as application No. PCT/IB2004/001408 on Apr. 8, 2004, now Pat. No. 8,283,380.

(60) Provisional application No. 60/462,205, filed on Apr. 11, 2003.

(51) Int. Cl.
| | |
|---|---|
| *A61K 31/137* | (2006.01) |
| *A61K 31/16* | (2006.01) |
| *A61K 31/167* | (2006.01) |
| *A61K 31/428* | (2006.01) |
| *A61K 31/49* | (2006.01) |
| *A61K 31/165* | (2006.01) |
| *A61K 31/4045* | (2006.01) |
| *A61K 31/473* | (2006.01) |
| *A61K 31/48* | (2006.01) |
| *A61K 31/498* | (2006.01) |
| *A61K 45/06* | (2006.01) |
| *A61K 31/4745* | (2006.01) |
| *A61K 31/475* | (2006.01) |
| *A61K 31/485* | (2006.01) |
| *A61K 31/4985* | (2006.01) |
| *A61K 31/55* | (2006.01) |

(52) U.S. Cl.
CPC ........... *A61K 31/165* (2013.01); *A61K 31/137* (2013.01); *A61K 31/16* (2013.01); *A61K 31/473* (2013.01); *A61K 31/475* (2013.01); *A61K 31/4745* (2013.01); *A61K 31/48* (2013.01); *A61K 31/485* (2013.01); *A61K 31/498* (2013.01); *A61K 31/4985* (2013.01); *A61K 31/55* (2013.01); *A61K 45/06* (2013.01)

(58) Field of Classification Search
CPC .. A61K 31/137; A61K 31/16; A61K 31/167; A61K 31/428; A61K 31/49; A61K 31/165; A61K 31/4045
See application file for complete search history.

(56) References Cited

U.S. PATENT DOCUMENTS

| | | | |
|---|---|---|---|
| 3,795,739 | A | 3/1974 | Birkmayer et al. |
| 4,049,663 | A | 9/1977 | Harper et al. |
| 4,513,009 | A | 4/1985 | Roques et al. |
| 4,935,429 | A | 6/1990 | Dackis et al. |
| 4,970,200 | A | 11/1990 | Birkmayer et al. |
| 5,017,607 | A | 5/1991 | Chiesi |
| 5,236,957 | A | 8/1993 | Dostert et al. |
| 5,391,577 | A | 2/1995 | Dostert et al. |
| 5,502,079 | A | 3/1996 | Dostert et al. |
| 5,945,454 | A | 8/1999 | Pevarello et al. |
| 6,217,905 | B1 | 4/2001 | Edgren et al. |
| 6,258,827 | B1 | 7/2001 | Chenard et al. |
| 6,306,903 | B1 | 10/2001 | Pevarello et al. |
| 6,500,867 | B1 | 12/2002 | Virkki et al. |
| 2002/0019421 | A1 | 2/2002 | Biberman |

FOREIGN PATENT DOCUMENTS

| | | |
|---|---|---|
| EP | 0400495 A1 | 12/1990 |
| GB | 1140748 | 1/1969 |
| WO | WO 90/14334 A1 | 11/1990 |
| WO | WO 94/22808 A1 | 10/1994 |
| WO | WO 97/05102 A1 | 2/1997 |

OTHER PUBLICATIONS

Andringa, G. et al., "TCH346 prevents motor symptoms and loss of striatal FDOPA uptake in bilaterally MPTP-treated primates," Neurobiol. Dis. 14:205-217 (2003) (Exhibit 72).
Anonymous: "Newron Releases Positive Preliminary Phase II Data for Safinamide in Parkinson's Disease" Press Release of Jan. 9, 2003, Retrieved from the Internet: URL: http://www.newron.com/uploads/SafinamidePhaseIIdataFinal090103.pdf retrieved on Feb. 18, 2009.
Archer, T. et al., 2002, "Restorative Effects of Glumate Antagonists in Experimental Parkinsonism," Amino Acids, 23:71-85.
Bailey et al., 1975, "The Mechanism of Action of Amantadine in Parkinsonism: A Review," Arch. Int. Pharmacodyn. Ther., 216: 246-262.

(Continued)

*Primary Examiner* — Sahar Javanmard
(74) *Attorney, Agent, or Firm* — Silvia Salvadori, P.C.; Silvia Salvadori

(57) ABSTRACT

New uses of safinamide, safinamide derivatives and MAO-B inhibitors in novel types of treatment for Parkinson's Disease are described. More specifically, the invention relates to methods for treating Parkinson's Disease through the administration of safinamide, a safinamide derivative, or a MAO-B inhibitor, in combination with other Parkinson's Disease agents or treatments, such as levodopa/PDI or dopamine agonists.

16 Claims, No Drawings

(56) References Cited

OTHER PUBLICATIONS

Benedetti, M. S. et al., 1994, "The Anticonvulsant FCE 26743 is a Delective and Short-Acting MAO-B Inhibitor Devoid of Inducing Properties Towards Cytochrone P450-dependent Testosterone Hydroxylation in Mice and Rats," J. Pharm. Pharmacol. 46:814-819.
Calne, D. B. et al., "Manganism and Idiopathic Parkinsonism, Similarities and Differences," Neurology 44:1583-1586 (1994).
Chase, Thomas, 1998, "The Significance of Continuous Dopaminergic Stimulation in the Treatment of Parkinson's Disease, " Drugs, 55 (Suppl. 1): 1-9.
Chaudhuri, K. R. et al., "International multicenter pilot study of the first comprehensive self-completed nonmotor symptoms questionnaire for Parkinson's disease: the NMSQuest study," Movement Disorders 21:916-923 (2006) (Exhibit 47).
Chauduri, K. R. et al., "The metric properties of a novel non-motor symptoms scale for Parkinson's disease: results from an international pilot study," Movement Disorders 22:1901-1911 (2007) (Exhibit 45).
Chazot, P., 2001, "Salfinamide, Newron Pharmaceuticals," Current Opinion in Invest. Drugs, 2(6): 809-813.
Cho, C. et al., "A model-based approach for assessing Parkinsonian gait and effects of levodopa and deep-brain stimulation," IEEE Engineering in Medicine and Biology Society Conference Proceedings, 1228-1231 (2006) (Exhibit 48).
Clarke, C. E., 2002, "Medical Management of Parkinson's Disease," J Neurol Neurosurg Psychiatry 72 (Suppl. 1) i22-i27.
Communication for European Patent Application 04 726 590.5-2123 mailed Dec. 5, 2006.
*Curriculum Vitae* of C. Warren Olanow, M.D., FRCPC (Exhibit 69).
DuBois, B. et al., "Diagnostic Procedures for Parkinson's disease dementia: Recommendations from the Movement Disorder Society Task Force," Movement Disorders 22:2314-2324 (2007) (Exhibit 44).
Emre, M. et al., "Clinical diagnostic criteria for dementia associated with Parkinson's disease," Movement Disorders 22:1689-1707 (2007) (Exhibit 43).
Facca, A, et al., 2003, "Differential Diagnosis of Parkinsonism," Adv. Neurol, 91:383-396.
Fahn, S., Parkinson Study Group, "Levodopa and the progression of Parkinson disease," N. Eng. J. Med. 351: 2498-2508 (2004) (Exhibit 2).
Fariello et al., 1998, "Preclinical Evaluation of PNU-151774E as a Novel Anticonvulsant," J. Pharmacol. Exp. Ther. 285: 397-403.
Fredriksson et al., "Effects of co-administration of anticonvulsant and putative anticonvulsive agents and sub-suprathreshold doses of L-Dopa upon motor behavior of MPTP-treated mice", Journal of Neural Transmission, vol. 103, Nos. 9-10, Oct. 1999, pp. 889-909.
Freeman, T. B. et al., "Bilateral fetal nigral transplantation into the postcommissural putamen in Parkinson's Disease," Ann. Neurol. 38:379-388 (1995) (Exhibit 39).
Freeman, T. B. et al., "Use of placebo surgery in a controlled trial of a cellular-based therapy for Parkinson's disease," N. Engl. J. Med. 341:988-992 (1999) (Exhibit 32).
Germano, I. M. et al., "Unilateral stimulation of the subthalamic nucleus in Parkinson's disease: a double blind 12-month study," J. Neurosurgery 101:36-42 (2004) (Exhibit 26).
Goetz, C. G. et al., "Movement Disorder Society-sponsored revision of the Unified Parkinson's Disease Rating Scale (MDS-UPDRS): scale presentation and clinimetric testing results," Movement Disorders 23:2129-2170 (2008) (Exhibit 41).
Goetz, C. G. et al., "Sarizotan as a treatment for dyskinesias in Parkinson's disease: a double-blind placebo-controlled trial," Movement Disorders 22:179-186 (2007) (Exhibit 18).
Goetz C. G. et al., "Movement disorder society-sponsored revision of the Unified Parkinson Disease Rating Scale (MDS-UPDRS): Process, format and clinimetric testing plan," Movement Disorders 22:41-47 (2007) (Exhibit 46).
Good, P. F. et al., "Neuromelanin-containing neurons of the substantia nigra accumulate iron and aluminum in Parkinson's disease: A LAMMA study," Brain Res. 593:343-346 (1992) (Exhibit 62).
Hauser, R. A. et al., "Blood manganese correlates with brain magnetic resonance imaging changes in patients with liver disease," Can. J. Neurol. Sci. 23:95-98 (1996) (Exhibit 59).
Hauser, R. A. et al., "Long-term evaluation of bilateral fetal nigral transplantation in Parkinson disease," Arch. Neurol. 56(2):179-87 (1999) (Exhibit 31).
Heikkila, R. et al., 1984, "Protection Against the Dopaminergic Neurotoxicity of 1-Methyl-4-Phenyl-1,2,5,6-Tetrahydropyridine by Monoamine Oxidase Inhibitors," Nature 311: 467-469.
Hely et al., "The Sydney Multicenter Study of Parkinson's disease: The Inevitability of Dementia at 20 years," *Mov. Disord* . 6:837-844 (2008). (Exhibit H to 3$^{rd}$ Declaration of C. Warren Olanow).
Huang, C. et al., "Progression after chronic manganese exposure," Neurology 43:1479-1483 (1993) (Exhibit 64).
International Preliminary Examination Report and Written Opinion of PCT/IB2004/001408 (2005).
International Search Report of PCT/IB2004/001408 (2004).
Jenner, P. et al., "Oxidative stress and the pathogenesis of Parkinson's disease," Neurology 47 (suppl 3):161-170 (1996) (Exhibit 58).
Koller, W. et al., "High frequency unilateral thalamic stimulation in the treatment of essential and Parkinsonian tremor," Ann. Neurol. 42:292-299 (1997) (Exhibit 24).
Kordower, J. H. et al., "Functional fetal nigral grafts in a patient with Parkinson's disease: chemoanatomic, quantitative, ultrastructural, and metabolic studies," J. Comparative Neurol. 370:203-230 (1996) (Exhibit 37).
Kordower, J. H. et al., "Dopaminergic transplants in patients with Parkinson's disease: neuroanatomical correlates of clinical recovery," Exp. Neurology 144:41-46 (1997) (Exhibit 35).
Kordower, J. H. et al., "Fetal grafting for Parkinson's disease: expression of immune markers in two patients with functional fetal nigral implants," Cell. Transp. 6: 213-219 (1997) (Exhibit 34).
Kordower, J. H. et al., "Fetal nigral grafts survive and mediate clinical benefit in a patient with Parkinson's disease," Movement Disorders 13(3):383-93 (1998) (Exhibit 33).
Kordower, J. H. et al., "Lewy body-like pathology in long-term embryonic nigral transplants in Parkinson's disease," Nature Med. 14:504-506 (2008) (Exhibit 29).
Kordower, J. H. et al., "Neuropathologic evidence of graft survival and striatal reinnervation after the transplantation of fetal mesencephalic tissue in a patient with Parkinson's disease," N. Engl. J. Med. 332:1118-1124 (1995) (Exhibit 38).
Kordower, J. H. et al., "Transplanted dopaminergic neurons develop PD pathologic changes: a second case report," Movement Disorders 23:2303-2306 (2008) (Exhibit 28).
Lang et al., "Progress in Clinical Neurosciences: A Forum on the Early Management of Parkinson's Disease," Canadian J. Neurol. Sci. 32:277-286 (2005). (Exhibit E to 3$^{rd}$ Declaration of C. Warren Olanow).
Letter regarding Oral Proceedings for European Patent Application 04 726 590.5-2123 dated Oct. 19, 2007.
Lieberman, A. et al., "A multi-center trial of ropinirole as adjunct treatment for Parkinson's disease," Neurology 51:1057-1062 (1998) (Exhibit 8).
Macleod et al., "Monoamine oxidase B inhibitors for early Parkinson's disease (review)," Cochrane Database of Systematic Reviews 2005, Issue 3, Art. No. CD004898. (Exhibit A to 3$^{rd}$Declaration of C. Warren Olanow).
Maj, R. et al., 1999, "PNU-141774E, A Combined Mao-B and Glutamate Release Inhibitor, is Effective in Animal Models of Parkinson's Disease," Society for Neuroscience, vol. 25, p. 1599.
Mann et al., 1971, "Amantadine for Parkinson's Disease, " Neurology, 21: 958-962.
Marjarna-Lyons, J. et al., 2001, "Parkinson's Disease: Update in Daignosis and Symptom Management," Geriatrics Aug.; 56(8):24-25, 29-30, and 33-35.
Marks, W. J. et al., "Safety and tolerability of intraputaminal delivery of CERE-120 (adeno-associated virus serotype

(56) References Cited

OTHER PUBLICATIONS 2-neurturin) to patients with idiopathic Parkinson's disease: an open-label, phase I trial," Lancet Neurol. 7:400-408 (2008) (Exhibit 40).
Marsden et al; 1997, "Success and Problems of Long-Term Levodopa Therapy in Parkinson's Disease," Lancet Feb. 12, 1997: 345-349.
Martinez-Martin, P. et al., "Prevalence of nonmotor symptoms in Parkinson's disease in an international setting: study using nonmotor symptoms questionnaire in 545 patients," Movement Disorders 22:1623-1629 (2007) (Exhibit 42).
McCall et al., "Sumanirole, a Highly Dopamine $D_2$-Selective Receptor Agonist: In Vitrol and in Vivo Pharmacological Characterization and Efficacy in Animal Models of Parkinson's Disease," The Journal of Pharmacology and Experimental Therapeutics, vol. 314, No. 3, pp. 1248-1256 (2005). (Exhibit D to Second Declaration of C. Warren Olanow Under 37 C.F.R. § 1.132).
McNaught, K. et al., "Failure of the ubiquitin-proteasome system in Parkinson's disease," Nature Reviews Neuroscience 2: 589-594 (2001) (Exhibit 54).
McNaught, K. et al., "Impairment of the ubiquitin-proteasome system causes dopaminergic cell death and inclusion body formation in ventral mesencephalic cultures," J. Neurochem 81: 301-306 (2002) (Exhibit 52).
McNaught, K. et al., "Proteasomal dysfunction in sporadic Parkinson's disease," Neurology 66(10 Suppl 4):S37-49 (2006) (Exhibit 49).
McNaught, K. et al., "Proteasomal inhibition causes nigral degeneration with inclusion bodies in rats," NeuroReport 13:1437-1441 (2002) (Exhibit 53).
McNaught, K. et al., "Proteasome inhibitior-induced model of Parkinson's disease," Ann. Neurol. 60:243-247 (2006) (Exhibit 55).
McNaught, K. et al., "Systemic exposure to proteasome inhibitors causes a progressive model of Parkinson's disease," Ann. Neurol. 56:149-162 (2004) (Exhibit 56).
Meldrum, B., 1994, "The Role of Glutamate in Epilepsy and Other CNS Disorders," Neurology, 44 (Supp. 8) 814-823.
Minutes of Oral Hearing (Jan. 25, 2008) for EP 04 726 590.5-2123.
Morrison, C. E. et al., "A program for neuropsychological investigation of deep brain stimulation (PNIDBS) in movement disorder patients: development, feasibility, and preliminary data," Neuropsychiatry, Neuropsychol. Behav. Neurol. 13:204-219 (Exhibit 23) (2000).
Mytilineou, C. et al., "Inhibition of Proteasome Activity Sensitizes Dopamine Neurons to Protein Alterations and Oxidative Stress," J. Neural Transmission 111:1237-1251 (2004) (Exhibit 51).
Mytilineou, C. et al, "L-(−)-desmethylselegiline, a metabolite of selegiline [L-(−)-deprenyl], protects mesencephalic dopamine neurons from excitotoxicity in vitro," J. Neurochem. 68:434-436 (1997) (Exhibit 76).
Mytilineou, C. et al., 1997, "L-Deprenyl Protects Mesencephalic Dopamine Neurons from Glutamate Receptor-Mediated Toxicity In Vitro," J. Neurochem. 68: 33-39.
Nair, V. D. et al., "P53 mediates non-transcriptional cell death in dopaminergic cells in response to proteasome inhibitors," J. Biol. Chem. 281:39550-39560 (2006) (Exhibit 50).
Newron Pharmaceuticals S.p.A. Announces Data of Phase I Clinical Trials of its Anti-epileptic and Anti-Parkinson Compound NW-1015, Press Release of Mar. 14, 2000, Retrieved from the Internet: URL: http://www.newron.com/uploads/AnnouncesdataofphaseIclinicaltrials.pdf; retrieved on Feb. 18, 2009.
Newron Pharmaceuticals SpA, "Safinamide: Study 018 Top-Line Results," Investor and Analyst Call Presentation, Nov. 4, 2010 (available online at http://www.newron.com) ("Study 018 Presentation"). (Exhibit F to $3^{rd}$ Declaration of C. Warren Olanow).
Olanow et al., "Modeling Parkinson's Disease," Annals of Neurology, vol. 66, No. 4, pp. 432-436 (2009). (Exhibit B to Second Declaration of C. Warren Olanow Under 37 C.F.R. § 1.132).
Olanow et al., "Parkinson's Disease and Other Movement Disorders," Chapter 372, in *Harrison's Principles of Internal Medicine*, 18th ed. (in press) (manuscript). (Exhibit G to $3^{rd}$ Declaration of C. Warren Olanow) (2006).
Olanow et al., "The scientific and clinical basis for the treatment of Parkinson disease (2009)," Neurology, vol. 72 (Supple 4), pp. S1-S136 (2009). (Exhibit A to Second Declaration of C. Warren Olanow Under 37 C.F.R. § 1.132).
Olanow, "Levodopa/Dopamine Replacement Strategies in Parkinson's Disease—Future Directions," Mov. Disord. 23(Suppl. 3): S613-S622 (2008). (Exhibit C to $3^{rd}$ Declaration of C. Warren Olanow).
Olanow, C. W. et al., "Tolcapone: An Efficacy and Safety Review (2007)," J. Clin. Neuropharm 30:287-294 (2007) (Exhibit 10).
Olanow, C. W. et al., "A double-blind controlled trial of bilateral fetal nigral transplantation in Parkinson's disease," Ann Neurol. 54(3):403-14 (2003) (Exhibit 30).
Olanow, C. W. et al., "A multi-center, double-blind, placebo-controlled trial of pergolide as an adjunct to Sinemet in Parkinson's disease," Movement Disorders 9: 40-47 (1994) (Exhibit 77).
Olanow, C. W. et al., "A randomized, double-blind, placebo-controlled, delayed start study to assess rasagiline as a disease modifying therapy in Parkinson's disease (the ADAGIO study): rationale, design, and baseline characteristics," Movement Disorders 23:2194-2201 (2008) (Exhibit 13).
Olanow, C. W. et al., "An open multi-center trial of Sinemet CR in levodopa naïve Parkinson's disease patients," Clin. Neuropharm. 14:235-240 (1991) (Exhibit 3).
Olanow, C. W. et al., "Clinical pattern and risk factors for dyskinesias following fetal nigral transplantation in Parkinson's disease: a double-blind video-based analysis," Movement Disorders 24:336-343 (2009) (Exhibit 27).
Olanow, C. W. et al., "CV205-502: Safety, tolerance to, and efficacy of increasing doses in patients with Parkinson's disease in a double-blind placebo crossover study," Clinical Neuropharm. 12:490-497 (1989) (Exhibit 15).
Olanow, C. W. et al., "Double-blind controlled study of pergolide mesylate as an adjunct to Sinemet in the treatment of Parkinson's disease," Adv. in Neurol. 45:555-560 (1987) (Exhibit 4).
Olanow, C. W. et al., "Double-blind controlled study of pergolide mesylate in the treatment of Parkinson's disease," Clinical Neuropharm. 10:178-185 (1987) (Exhibit 5).
Olanow, C. W. et al., "Double-blind, placebo-controlled study of entacapone in levodopa-treated patients with stable Parkinson's disease," Arch. Neurol. 61:1563-1568 (2004) (Exhibit 11).
Olanow, C. W. et al., "Fetal nigral transplantation as a therapy for Parkinson's disease," Trends. Neurosci. 19:102-109 (1996) (Exhibit 36).
Olanow, C. W. et al., "Free Radicals and Neurodegeneration," Trends Neurosci. 17: 193-194 (1994) (Exhibit 65).
Olanow, C. W. et al., "Multicenter, open-label, trial of Sarizotan in Parkinson disease patients with levodopa-induced dyskinesias (the SPLENDID study)," Clin. Neuropharm. 27:58-62 (2004) (Exhibit 17).
Olanow, C. W. et al., "TCH346 as a neuroprotective drug in Parkinson's disease: a double-blind, randomised, controlled trial," Lancet Neurol. 5:1013-1020 (2006) (Exhibits 16 and 73).
Olanow, C. W. et al., "The effect of deprenyl and levodopa on the progression of Parkinson's disease," Ann. Neurol 38: 771-777 (1995) (Exhibit 78).
Olanow, C. W. et al., "The role of deep brain stimulation as a surgical treatment for Parkinson's disease," Neurology 55 (suppl. 6):60-66 (2000) (Exhibit 25).
Olanow, C. W., "An Introduction to the Free Radical Hypothesis in Parkinson's Disease," Ann. Neurol. 32:2-9 (1992) (Exhibit 61).
Olanow, C. W., (for the Tasmar advisory board), "Tolcapone and hepatotoxic effects," Arch. Neurol. 57:263-267 (2000) (Exhibit 9).
Parkes, J. D, et al., 1971, Treatment of Parkinson's Disease with Amantadine and Levodopa,: Lancet, 21: 1083-1086.
Parkinson Study Group (C.W. Olanow, Steering Committee), "Effect of Deprenyl on the progression of disability in early Parkinson's disease," N. Engl. J. Med. 321:1364-1371 (1989) (Exhibit 6).

(56) References Cited

OTHER PUBLICATIONS

Parkinson Study Group (C.W. Olanow, Steering Committee), "Safety and efficacy of pramipexole in early Parkinson's disease: a randomized dose-ranging study," JAMA 278:125-130 (1997) (Exhibit 7).
Parkinson Study Group (Olanow CW, Steering Committee), "A controlled clinical trial of lazabemide (Ro 19-6327) in untreated Parkinson's disease," Ann. Neurol. 33:350-356 (1993) (Exhibit 19).
Parkinson Study Group (Olanow CW, Steering Committee), "A controlled trial of lazabemide (Ro 19/6327) in levodopa treated Parkinson's disease," Arch. Neurol. 51:342-347 (1994) (Exhibit 20).
Parkinson Study Group (Olanow CW, Steering Committee), "Effect of lazabemide on the progression of disability in early Parkinson's disease," Ann. Neurol. 40:99-107 (Exhibit 21), (1996).
Parkinsons Study Group, Olanow, C.W., Steering Committee, "Effects of tocopherol and deprenyl on the progression of disability in early Parkinson's disease," N. Eng. J. Med. 328:176-183 (1993) (Exhibit 75).
Poewe, W., 1993, "Clinical Features, Diagnosis, and Imaging of Parkinsonian Syndromes," Curr Opin Neurol Neurosurg, Jun., 6(3):333-338.
Remington's Pharmaceutical Sciences 15th Edition, pp. 1035-1038 and 1570-1580 (1975).
Reply to Examination Report for European Patent Application 04 726 590.5-2123 dated Aug. 9, 2006.
Reply to Examination Report for European Patent Application 04 726 590.5-2123 dated Apr. 6, 2007.
Salvati, P. et al., 1999, "Biochemical and Electrophysiological Studies on the Mechanism of Action of PNU-151774E, A Novel Antiepileptic Compound," Pharmacol. Exp. Ther. 288:1151-1159.
Schwartz, A. M. et al., "Double-blind controlled study of MK-486," Transactions of the Amer. Neurol. Ass'n 98:301-303 (1973) (Exhibit 1).
Sengstock, G. J. et al., "Infusion of iron into the rat substantia nigra: nigral pathology and dose-dependent loss of striatal dopaminergic markers," J. Neurosci. Res. 35:67-82 (1993) (Exhibit 63).
Sengstock, G. J. et al., "Intranigral iron infusion in the rat. Acute elevations in nigral lipid peroxidation and striatal dopaminergic markers with ensuing nigral degeneration," Biol. Trace Elem. Res. 58:177-195 (1997) (Exhibit 57).
Sengstock, G. J. et al., "Progressive changes in striatal dopaminergic markers, nigral volume, and rotational behavior following iron infusion into the rat substantia nigra," Exp. Neurol. 130:82-94 (1994) (Exhibit 68).
Shinotoh, H. et al., "MRI and PET studies of manganese-intoxicated monkeys," Neurology 45:1199-1204 (1995) (Exhibit 67).
Siderowf, A., 2001, "Parkinson's Disease: Clinical Features, Epidemiology, and Genetics," Movement Disorders, Aug., 19(3):565-578.
Smith, L. A. et al., "Multiple small doses of levodopa plus entacapone produce continuous dopaminergic stimulation and reduce dyskinesia induction in MPTP-treated drug-naive primates," Movement Disorders 20:306-314 (2005) (Exhibit 71).
Stern, M. B. et al., "A double-blind, randomized controlled trial of rasagiline as monotherapy in early Parkinson's disease patients," Movement Disorders 19:916-923 (2004) (Exhibit 12).
Stocchi et al., "Initiating Levodopa/Carbidopa Therapy With and Without Entacapone in Early Parkinson Disease: The STRIDE-PD Study," Ann. Neurol. 68:18-27 (2010). (Exhibit B to 3$^{rd}$ Declaration of C. Warren Olanow).
Stocchi F. et al., 2004, "Improvement of Motor Function in Early Parkinson Disease by Safinamide," Neurology 63(4):746-748.
Stocchi, F. et al., "Prospective randomized trial of lisuride infusion versus oral levodopa in patients with Parkinson's Disease," Brain 125:2058-2066 (2002) (Exhibit 14).
Stocchi, F. et al., 2006, Symptom Relief in Parkinson Disease by Safinamide: Biochemical and Clinical Evidence of Efficacy beyond MAO-B Inhibition; Neurology 67(7)SUPPL2:S24-S29.

Sulkava, R. 2003, "Differential Diagnosis between Early Parkinson's Disease and Dementia with Lewy Bodies," Adv. Neurol, 91:411-413.
Summons to Attend Oral Hearings for European Patent Application 04 726 590.5-2123 dated Jul. 2, 2007.
The Deep Brain Stimulation for PD Study Group (Obeso and Olanow, corresponding authors), "Deep brain stimulation of the subthalamic nucleus of the globus pallidus pars interna in Parkinson's disease," New Engl. J. Med. 345:956-963 (2001) (Exhibit 22).
Youdim, B. H. et al., 1991, "New Directions in Monoamine Oxidase A and B Selective Inhibitors and Substrates," Biochem. Pharmacol. 41(2): 155-162.
Barone, et al., 2013, "Safinamide as an Add-on Therapy to a Stable Dose of a Single Dopamine Agonist: Results from a Randomized, Placebo-Controlled, 24-Week Multicenter Trial in Early Idiopathic Parkinson Disease (PD) Patients (Motion study)" 65$^{th}$ AAN Annual Meeting in San Diego Abstract.
Schapira, et al., 2013, "Safinamide Add on to L-dopa: A randomized, Placebo-Controlled, 24-Week Global Trial in Patients with Parkinson's Disease (PD) and Motor Fluctuations (SETTLE)" 65$^{th}$ AAN Annual Meeting in San Diego Abstract.
Newron Pharmaceuticals & Zambon Company, "Safinamide Phase III study results present at 2013 MDPD meeting," Press release dated Apr. 22, 2013.
Borgohain et al., 2010, "Effect of safinamide on depressive symptoms in patients with mid-late stage Parkinson's disease," Poster 324, Movement Disorder Society 14th International Congress, Buenos Aires, Argentina 13-17.
Caccia et al., 2006 "Safinamide: from molecular targets to a new anti-Parkinson drug," Neurology 67 (suppl. 2) S18-S23.
Macleod et al., "Monoamine oxidase B inhibitors for early Parkinson's disease (review)," Cochrane Database of Systematic Reviews 2005, Issue 3, Art. No. CD004898.
Meshram et al., 2010, "Safinamide as add-on to levodopa improves motor function without worsening dyskinesia in patients with mid-late Parkinson's disease," Poster 359, Movement Disorder Society 14th International Congress, Buenos Aires, Argentina 13-17.
Oestreicher, E. et al, 1994, "Degeneration of nigrostriatal dopaminergic neurons increases iron within the substantia nigra: a histochemical and neurochemical study," Brain Res. 660: 8-18.
Olanow, et al., 2008, "Levodopa/Dopamine Replacement Strategies in Parkinson's Disease—Future Directions," Mov. Disord. 23(Suppl. 3): S613-S622.
Olanow et al., 2001, "An algorithm (decision tree) for the management of Parkinson's disease (2001): Treatment Guidelines," American Academy of Neurology (56):S1-588.
Olanow et al., 2006, "Continuous dopamine-receptor treatment of Parkinson's disease: scientific rationale and clinical implications," Lancet Neurology 5:677-687.
Rascol et al., 2002, "A 2-year, multicenter, placebo-controlled, double-blind, parallel group study of the effect of riluzole on Parkinson's disease progression," *Movement Disorders* 17 (Suppl. 5): S29.
Anand et al., 2013 "Safinamide is associated with clinically important improvement in motor symptoms in fluctuating PD patents as add-on to levodopa (SETTLE)," Movement Disorders 28 Suppl 1:422.
Schapira et al., 2013 "Safinamide significantly improves responder rates in fluctuatin Parkinson's disease (PD) patents as add-on to levodopa (STTLE)," Movement Disorders 28 Suppl 1:424.
Barone et al., 2013, "Safinamide add-on to a stable dose of a single dopamine agonist: results from a randomized, placebo-controlled, 24-week multi-center trial in early idiopathic Parkinson's disease (PD) patients (MOTION)," P01.061.
Calne et al., 1974, "Treatment of Parkinsonism with Bromocriptine," Lancet 2(7893):1355-56.
Farber Nuri B., 2003, "The NMDA receptor hypofunction model of psychosis," Ann N Y Acad Sci. 1003:119-30.
Frucht et al., 1999, "Falling asleep at the wheel: motor vehicle mishaps in persons taking pramipexole and ropinirole," Neurology 52:1908-1910.

(56) References Cited

OTHER PUBLICATIONS

Lundbeck, 2013, "New Data Show Azilect® (Rasagiline Tablets) Provided Clinical Benefit in Patients With Early Parkinson's When Added to Suboptimally Controlled Patients on Dopamine Agonist Therapy," H. Lundbeck A/S Press Release.

Olanow et al., 2001, "An algorithm (decision tree) for the management of Parkinson's disease (2001)," Neurology 56:1-88.

Olanow et al., 2006, "Continuous Dopamine Receptor Stimulation in the Treatment of Parkinson's Disease: Scientific Rationale and Clinical Implications," Lancet Neurology 5:677-687.

Olanow et al., 2013, "Factors predictive of the development of levodopa-induced dyskinesia and wearing-off in Parkinson's disease," Mov Disord 28:1064-1071.

Olanow et al., 2009, "Scientific and Clinical Basis for the treatment of PD—2009," Neurology 72 (21 Suppl 4): S1-136.

Obeso et al., 2000, "Levodopa motor complications in Parkinson's diseae," Trends Neurosci 23 (suppl): 2-7.

Rascol et al., 2006, "Development of dyskinesias in a 5-year trial of ropinirole and L-dopa," Mov Disord 21:1844-1850.

Schapira et al., 2013, "Long-term efficacy and safety of safinamide as add-on therapy in early Parkinson's disease," European Journal of Neurology 20: 271-280.

Stocchi et al., 2012, "A Randomized, Double-Blind, Placebo-Controlled Trial of Safinamide as Add-on Therapy in Early Parkinson's Disease Patients," Movement Disorders 27(1): 106-112.

Weintraub et al., 2010, "Impulse control disorders in Parkinson disease: a cross-sectional study of 3090 patients," Arch Neurol. 67:589-95.

METHODS FOR TREATMENT OF PARKINSON'S DISEASE

FIELD OF THE INVENTION

The invention relates to a new compositions and methods of treating Parkinson's disease. More specifically, the invention relates to methods for treating Parkinson's Disease through the administration of safinamide, safinamide derivative or a MAO-B inhibitor in combination with other Parkinson's Disease agents or treatments, such as dopamine agonists or levodopa.

BACKGROUND OF THE INVENTION

Parkinson's Disease (PD) currently affects about 10 million people world-wide. PD is a highly specific degeneration of dopamine-containing cells of the substantia nigra of the midbrain. Degeneration of the substantia nigra in Parkinson's disease causes a dopamine deficiency in the striatum. Effective management of a patient with PD is possible in the first 5-7 years of treatment, after which time a series of often debilitating complications, together referred to as Late Motor Fluctuations (LMF) occur (Marsden and Parkes, Lancet II: 345-349, 1997). It is believed that treatment with levodopa, or L-dopa, the most effective antiparkinson drug, may facilitate or even promote the appearance of LMF. Dopamine agonists are employed as a treatment alternative, but they do not offer the same degree of symptomatic relief to patients as L-dopa does (Chase, Drugs, 55 (suppl. 1): 1-9, 1998).

Symptomatic therapies improve signs and symptoms without affecting the underlying disease state. Levodopa ((−)-L-alpha-amino-beta-(3,4-dihydroxybenzene) propanoic acid) increases dopamine concentration in the striatum, especially when its peripheral metabolism is inhibited by a peripheral decarboxylase inhibitor (PDI). Levodopa/PDI therapy is widely used for symptomatic therapy for Parkinson's disease, such as combinations with llevodopa, with carbidopa ((−)-L-alpha-hydrazino-alpha-methyl-beta-(3,4-dihydroxybenzene) propanoic acid monohydrate), such as SINEMET®; levodopa and controlled release carbidopa (SINEMET-CR®), levodopa and benserazide (MADOPAR®, Prolopa), levodopa plus controlled release benserazide (2-Amino-3-hydroxy-propionic acid N'-(2,3,4-trihydroxy-benzyl)-hydrazide), MADOPAR-HBS.

COMT (catechol-O-methyltransferase) inhibitors enhance levodopa treatment as they inhibit levodopa's metabolism, enhancing its bioavailability and thereby making more of the drug available in the synaptic cleft for a longer period of time. Examples of COMT inhibitors include tolcapone (3,4-dihydroxy-4'-methyl-5-nitrobenzophenone) and entacapone ((E)-2-cyano-3-(3,4-dihydroxy-5-nitrophenyl)-N,N-diethyl-2-propenamide).

Dopamine agonists provide symptomatic benefit by directly stimulating post-synaptic striatal dopamine receptors. Examples include bromocriptine ((5α)-2-Bromo-12'-hydroxy-2'-(1-methylethyl)-5'-(2-methylpropyl)ergotaman-3',6',18-trione), pergolide (8B-[(Methylthio)methyl]-6-propylergoline), ropinirole (4-[2-(Dipropylamino)ethyl]-1,3-dihydro-2H-indol-2-one), pramipexole ((S)-4,5,6,7-Tetrahydro-$N^6$-propyl-2,6-benzothiazolediamine), lisuride (N'-[(8α)-9,10-didehydro-6-methylergolin-8-yl]-N,N-diethylurea), cabergoline ((8β)-N-[3-(Dimethylamino)propyl]-N-[(ethylamino)carbonyl]-6-(2-propenyl)ergoline-8-carboxamide), apomorphine ((6aR)-5,6,6a,7-Tetrahydro-6-methyl-4H-dibenzo[de,g]quinoline-10,11-diol), sumanirole (5-(methylamino)-5,6-dihydro-4H-imidazo {4,5,1-ij}quinolin-2(1H)-one), rotigotine ((−)(S)-5,6,7,8-tetrahydro-6-[propyl[2-(2-thienyl)ethyl]amino]-1-naphthol), talipexole (5,6,7,8-Tetrahydro-6-(2-propenyl)-4H-thiazolo[4,5-d]azepin-2-amine), and dihydroergocriptine (ergotaman-3',6',18-trione,9,10-dihydro-12'-hydroxy-2'-methyl-5'-(phenylmethyl)(5'α)). Dopamine agonists are effective as monotherapy early in the course of Parkinson's disease and as an adjunct to levodopa in more advanced stages. Unlike levodopa, dopamine agonists directly stimulate post-synaptic dopamine receptors. They do not undergo oxidative metabolism and are not thought to accelerate the disease process. In fact, animals fed a diet including pergolide were found to experience less age-related loss of dopamine neurons.

Amantidine (1-Aminotricyclo (3,3,1,1$^{3,7}$)decane) is an antiviral agent that was discovered by chance to have anti-parkinsonian activity. Its mechanism of action in PD has not been established, but it was originally believed to work by increasing dopamine release (Bailey et al., Arch. Int. Pharmacodyn. Ther., 216: 246-262, 1975). Patients who receive amantidine either as monotherapy or in combination with levodopa show improvement in akinesia, rigidity and tremor (Mann et al., Neurology, 21: 958-962, 1971; and Parkes et al., Lancet, 21: 1083-1086, 1971).

Other medications used in the treatment of Parkinson's disease include MAO-B inhibitors. Inhibition of L-dopa metabolism through inactivation of the monoamino oxidase type B (MAO-B) is an effective means of enhancing the efficacy of both endogenous residual dopamine and that exogenously derived from its precursor, L-dopa (Youdim and Finberg, Biochem Pharmacol. 41: 155-162, 1991). Selegiline (methyl-(1-methyl-2-phenyl-ethyl)-prop-2-ynyl-amine) is a MAO-B inhibitor. There is evidence that treatment with selegiline may slow down disease progression in PD by blocking the formation of free radicals derived from the oxidative metabolism of dopamine (Heikkila et al., Nature 311: 467-469, 1984; Mytilineou et al., J Neurochem., 68: 33-39, 1997). Another MAO-B inhibitor under development is rasagiline (N-propargyl-1-(R)aminoindan, TEVA Pharmaceutical Industries, Ltd.). Other examples of MAO B inhibitors include lazabemide (N-(2-Aminoethyl)-5-chloro-2-pyridinecarboxamide) and caroxazone (2-Oxo-2H-1,3-benzoxazine-3(4H)-acetamide).

SUMMARY OF THE INVENTION

The present invention is based, in part, on the unexpected finding that the combination of safinamide, a safinamide derivative, or a MAO-B inhibitor and other Parkinson's Disease agents provides a more effective treatment for Parkinson's Disease (PD) than either component alone. The invention includes methods of using such compounds to treat Parkinson's Disease and pharmaceutical compositions for treating PD which may be used in such methods.

In one embodiment, the invention relates to methods for treating Parkinson's Disease through the administration of safinamide, a safinamide derivative, or a MAO-B inhibitor in combination with other Parkinson's Disease agents or treatments, either alone or in combination, such as levodopa/PDI, COMT inhibitors, amantidine, or dopamine agonists. When safinamide is used in combination with other types of drugs, an unexpected, synergistic effect is achieved. The improvement of symptoms and the delay of disease progression are more evident in patients treated with the combination of drugs than those treated with a single type of drug alone. When safinamide was administered alone, patients improved only by an average 6.9% whereas when safinamide was added to a stabilized dose of a variety of dopamine agonists, the average improvement reached 27.8%.

In one embodiment, methods of treating Parkinson's Disease are disclosed, wherein safinamide, a safinamide derivative, or a MAO-B inhibitor and a Parkinson's Disease agent are administered to a subject having Parkinson's Disease, such that the Parkinson's Disease is treated or at least partially alleviated. The safinamide, a safinamide derivative, or a MAO-B inhibitor and Parkinson's Disease agent may be administered as part of a pharmaceutical composition, or as part of a combination therapy. The amount of safinamide, safinamide derivative, or a MAO-B inhibitor and a Parkinson's Disease agent is typically effective to reduce symptoms and to enable an observation of a reduction in symptoms.

Safinamide, or safinamide derivative, may be administered at a dosage of generally between about 0.1 and about 10 mg/kg/day, more preferably from about 0.5 to about 1, 2, 3, 4 or 5 mg/kg/day.

MAO-B inhibitors may be administered at a dosage of generally between about 0.1 mg/day and about 50 mg/day, more preferably from about 1 mg/day to about 10 mg/day.

Safinamide is an anti-PD agent with multiple mechanisms of action. One mechanism of safinamide may be as a MAO-B inhibitor. Other MAO-B inhibitors which may be used in the invention, in place of safinamide, include, but are not limited to, selegiline, rasagiline, lazabemide, and caroxazone, pharmaceutically acceptable salts and esters thereof, and combinations thereof.

Parkinson's Disease agents which may be used with safinamide, a safinamide derivative, or a MAO-B inhibitor in the pharmaceutical compositions, methods and combination therapies of the invention include one or more of levodopa/PDIs, dopamine agonists, amantidine and catechol-O-methyltransferase (COMT) inhibitors.

Levodopa/PDIs include, but are not limited to, levodopa plus carbidopa (SINEMET®), levodopa plus controlled release carbidopa (SINEMET-CR®), levodopa plus benserazide (MADOPAR®), and levodopa plus controlled release benserazide (MADOPAR-HBS).

Dopamine agonists include, but are not limited to, bromocriptine, pergolide, ropinirole, pramipexole, lisuride, cabergoline, apomorphine, sumanirole, rotigotine, talipexole and dihydroergocriptine.

COMT inhibitors include, but are not limited to, tolcapone and entacapone.

Combinations of safinamide, a safinamide derivative or MAO-B inhibitor and levodopa/PDI may also include additional Parkinson's Disease agents such as COMT inhibitors, amantidine and/or dopamine agonists. One combination which can be used in the pharmaceutical compositions, methods and combination therapies of the invention includes safinamide, a safinamide derivative or MAO-B inhibitor and levodopa/PDI. Another combination which can be used in the pharmaceutical compositions, methods and combination therapies of the invention includes safinamide or MAO-B inhibitor, levodopa/PDI, and a COMT inhibitor. Another combination which can be used in the pharmaceutical compositions, methods and combination therapies of the invention includes safinamide, a safinamide derivative, or MAO-B inhibitor, levodopa/PDI, and a dopamine agonist. Another combination which can be used in the pharmaceutical compositions, methods and combination therapies of the invention includes safinamide, a safinamide derivative or MAO-B inhibitor, levodopa/PDI, a COMT inhibitor, and a dopamine agonist. Yet another combination which can be used in the pharmaceutical compositions, methods and combination therapies of the invention includes safinamide, a safinamide derivative or MAO-B inhibitor, levodopa/PDI, a COMT inhibitor, a dopamine agonist, and amantidine.

In one aspect, a combination therapy for PD includes safinamide, a safinamide derivative (or a safinamide derivative) and a dopamine agonist. In one embodiment, a combination therapy for PD includes safinamide (or a safinamide derivative) and one or more of bromocriptine, cabergoline, lisuride, pergolide, ropinirole, apomorphine, sumanirole, rotigotine, talipexole, dihydroergocriptine, and pramipexole, for treating a patient in need of PD treatment.

In another aspect, a combination therapy for PD includes safinamide (or a safinamide derivative) and levodopa/PDI. In one embodiment a combination therapy for PD includes safinamide (or a safinamide derivative) and one or more of levodopa/PDIs such as levodopa plus carbidopa (SINEMET®), levodopa plus controlled release carbidopa (SINEMET-CR®), levodopa plus benserazide (MADOPAR®), levodopa plus controlled release benserazide (MADOPAR-HBS) for treating a patient in need of PD treatment.

In another aspect, a combination therapy for PD includes safinamide (or a safinamide derivative), levodopa/PDI, and a COMT inhibitor. In an embodiment, a combination therapy for PD includes safinamide (or a safinamide derivative), one or more of levodopa/PDIs such as levodopa plus carbidopa (SINEMET®), levodopa plus controlled release carbidopa (SINEMET-CR®), levodopa plus benserazide (MADOPAR®), levodopa plus controlled release benserazide (MADOPAR-HBS) and one or more of entacapone and tolcapone, for treating a patient in need of PD treatment.

In an aspect, a combination therapy for PD includes safinamide (or a safinamide derivative), levodopa/PDI, a COMT inhibitor, and a dopamine agonist for treating a patient in need of PD treatment. In an embodiment, a combination therapy for PD includes safinamide (or a safinamide derivative), one or more of levodopa/PDIs such as levodopa plus carbidopa (SINEMET®), levodopa plus controlled release carbidopa (SINEMET-CR®), levodopa plus benserazide (MADOPAR®), levodopa plus controlled release benserazide (MADOPAR-HBS), one or more of entacapone and tolcapone, and one or more of bromocriptine, cabergoline, lisuride, pergolide, ropinirole, apomorphine, sumanirole, rotigotine, talipexole, dihydroergocriptine, and pramipexole, for treating a patient in need of PD treatment.

In an aspect, a combination therapy for PD includes safinamide (or a safinamide derivative), levodopa/PDI a COMT inhibitor, a dopamine agonist and amantidine for treating a patient in need of PD treatment. In an embodiment, a combination therapy for PD includes safinamide, amantidine, one or more of levodopa/PDIs such as levodopa plus carbidopa (SINEMET®), levodopa plus controlled release carbidopa (SINEMET-CR®), levodopa plus benserazide (MADOPAR®), levodopa plus controlled release benserazide (MADOPAR-HBS), and one or more of entacapone and tolcapone, one or more of bromocriptine, cabergoline, lisuride, pergolide, ropinirole, apomorphine, sumanirole, rotigotine, talipexole, dihydroergocriptine, and pramipexole, for treating a patient in need of PD treatment.

In one aspect, a combination therapy for PD includes one or more MAO-B inhibitors and a dopamine agonist. In one embodiment, a combination therapy for PD includes one or more of selegiline, rasagiline, lazabemide, and caroxazone and one or more of bromocriptine, cabergoline, lisuride, pergolide, ropinirole, apomorphine, sumanirole, rotigotine, talipexole, dihydroergocriptine, and pramipexole, for treating a patient in need of PD treatment.

In another aspect, a combination therapy for PD includes one or more MAO-B inhibitors and levodopa/PDI. In one embodiment, a combination therapy for PD includes one or more of selegiline, rasagiline, lazabemide, and caroxazone and one or more of levodopa plus carbidopa (SINEMET®), levodopa plus controlled release carbidopa (SINEMET-CR®), levodopa plus benserazide (MADOPAR®), levodopa plus controlled release benserazide (MADOPAR-HBS).

In another aspect, a combination therapy for PD includes one or more MAO-B inhibitors, levodopa/PDI and a COMT inhibitor. In an embodiment, a combination therapy for PD includes one or more of selegiline, rasagiline, lazabemide, and caroxazone, one or more of levodopa plus carbidopa (SINEMET®), levodopa plus controlled release carbidopa (SINEMET-CR®), levodopa plus benserazide (MADOPAR®), levodopa plus controlled release benserazide (MADOPAR-HBS), and one or more of entacapone and tolcapone for treating a patient in need of PD treatment.

In an aspect, a combination therapy for PD includes one or more MAO-B inhibitors, levodopa/PDI a COMT inhibitor and a dopamine agonist for treating a patient in need of PD treatment. In an embodiment, a combination therapy for PD includes one or more of selegiline, rasagiline, lazabemide, and caroxazone, one or more of levodopa plus carbidopa (SINEMET®), levodopa plus controlled release carbidopa (SINEMET-CR®), levodopa plus benserazide (MADOPAR®), levodopa plus controlled release benserazide (MADOPAR-HBS), one or more of entacapone and tolcapone, and one or more of bromocriptine, cabergoline, lisuride, pergolide, ropinirole, apomorphine, sumanirole, rotigotine, talipexole, dihydroergocriptine, and pramipexole, for treating a patient in need of PD treatment.

In an aspect, a combination therapy for PD includes one or more MAO-B inhibitors, levodopa/PDI, a COMT inhibitor, a dopamine agonist, and amantidine for treating a patient in need of PD treatment. In an embodiment, a combination therapy for PD includes one or more of selegiline, rasagiline, lazabemide, and caroxazone, amantidine, one or more of levodopa plus carbidopa (SINEMET®), levodopa plus controlled release carbidopa (SINEMET-CR®), levodopa plus benserazide (MADOPAR®), levodopa plus controlled release benserazide (MADOPAR-HBS), one or more of entacapone and tolcapone, and one or more of bromocriptine, cabergoline, lisuride, pergolide, ropinirole, apomorphine, sumanirole, rotigotine, talipexole, dihydroergocriptine, and pramipexole, for treating a patient in need of PD treatment.

Administration of the therapies and combination therapies of the invention may be orally, topically, subcutaneously, intramuscularly, or intravenously.

The invention further relates to kits for treating patients having Parkinson's Disease. Such kits include a therapeutically effective dose of an agent for treating or at least partially alleviating the symptoms of Parkinson's Disease (e.g., levodopa plus carbidopa (SINEMET®), levodopa plus controlled release carbidopa (SINEMET-CR®), levodopa plus benserazide (MADOPAR®), levodopa plus controlled release benserazide (MADOPAR-HBS), bromocriptine, pergolide, ropinirole, pramipexole, lisuride, cabergoline, apomorphine, sumanirole, rotigotine, talipexole, dihydroergocriptine, entacapone, tolcapone, amantidine) and safinamide (or a safinamide derivative), or a MAO-B inhibitor such as selegiline, rasagiline, lazabemide, or caroxazone, either in the same or separate packaging, and instructions for its use.

Pharmaceutical compositions including safinamide, a safinamide derivative or a MAO-B inhibitor and a Parkinson's Disease agent, in an effective amount(s) to treat Parkinson's Disease, are also included in the invention.

DETAILED DESCRIPTION OF THE INVENTION

The features and other details of the invention will now be more particularly described and pointed out in the claims. It will be understood that particular embodiments described herein are shown by way of illustration and not as limitations of the invention. The principal features of this invention can be employed in various embodiments without departing from the scope of the invention.

Safinamide, (+)-(S)-2-[[p-[(m-fluorobenzyl)oxy]-benzyl]amino]propionamide, (NW-1015, FCE26743 or PNU151774E), is an α-aminoamide, a chemical class of compounds with a favorable pharmacological and safety profile. Safinamide and its analogs or derivatives are thought to be multi-mechanism drugs which potentially exert biological activity via a variety of mechanisms, including sodium and a calcium channel blockade and dopamine re-uptake inhibition (Fariello et al., J. Pharmacol. Exp. Ther. 285: 397-403, 1998; Salvati et al, J. Pharmacol. Exp. Ther. 288:1151-1159, 1999; U.S. Pat. Nos. 5,236,957; 5,391,577; 5,502,079; 5,502,658; 5,945,454; 6,306,903, and PCT publications WO 90/14334; WO 97/05102 WO 99/35125. Safinamide is also a potent, reversible inhibitor of MAO-B activity (Strolin Benedetti et al., J. Pharm. Pharmacol. 46:814-819, 1994). Safinamide has been shown to be an anticonvulsant and neuroprotectant and it is under clinical development by oral route as anticonvulsant and anti-Parkinson agent.

Other N-substituted α-amino carboxamide derivatives have favorable pharmacological properties, for example, the treatment and prophylaxis of such diseases as coronary artery disease and atherosclerosis; moreover they are useful in the treatment of inflammatory conditions such as rheumatoid arthritis. British patent No. 1140748. Further substituted amino acid derivatives are known as enkephalinase inhibitors, analgesics and hypotensives. EP-A-0038758. Still other substituted glycine and alanine derivatives are disclosed by U.S. Pat. No. 4,049,663. The compounds according to this document have utility as oral analgesics.

Certain N-phenylalkyl substituted α-amino carboxamide derivatives, including safinamide, are described as active as anti-epileptic, anti-Parkinson, neuroprotective, antidepressant, antispastic, and/or hypnotic agents. See, e.g., U.S. Pat. Nos. 5,236,957; 5,391,577; 5,502,079; and PCT Publication WO 90/14334.

Thus, the use of such N-phenylalkyl substituted α-amino carboxamide compounds, e.g., safinamide derivatives, in the methods and compositions of the invention is contemplated.

Safinamide derivatives include those described by Formula I:

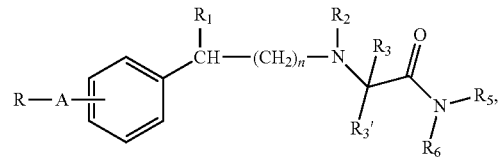

Formula I

Where:

R is $C_1$-$C_8$ alkyl; a $C_3$-$C_8$ cycloalkyl, furyl, thienyl or pyridyl ring; or a phenyl ring unsubstituted or substituted by 1 to 4 substituents independently chosen from halogen, $C_1$-$C_6$ alkyl, $C_1$-$C_6$ alkoxy and trifluoromethyl;

A is a —$(CH_2)_m$— or —$(CH_2)_p$—X—$(CH_2)_q$— group, wherein m is an integer of 1 to 4, one of p and q is zero and the other is zero or an integer of 1 to 4, and X is —O—, —S— or —$NR_4$— in which $R_4$ is hydrogen or $C_1$-$C_4$ alkyl; n is zero or 1;

each of $R_1$ and $R_2$, independently, is hydrogen or $C_1$-$C_4$ alkyl;

$R_3$ is hydrogen, $C_1$-$C_4$ alkyl unsubstituted or substituted by hydroxy or by a phenyl ring optionally substituted by 1 to 4 substituents independently chosen from halogen, $C_1$-$C_6$ alkyl, $C_1$-$C_6$ alkoxy and trifluoromethyl;

$R_{3'}$ is hydrogen; or $R_3$ and $R_{'3}$ taken together with the adjacent carbon atom form a $C_3$-$C_6$ cycloalkyl ring;

each of $R_5$ and $R_6$, independently, is hydrogen or $C_1$-$C_6$ alkyl; and wherein when R is $C_1$-$C_8$ alkyl, then A is a —$(CH_2)_p$—X—$(CH_2)_q$— group in which p and q are both zero and X is as defined above.

The present invention includes all the possible optical isomers of the compounds of formula (I) and their mixtures, as well as the metabolites of the compounds of formula (I). The present invention also includes within its scope pharmaceutically acceptable bioprecursors and prodrugs of the compounds of formula (I), i.e. compounds, which have a formula different to formula (I), but which nevertheless are directly or indirectly converted in vivo into a compound of formula (I) upon administration to a human being.

Pharmaceutically acceptable salts of the compounds of formula (I) include acid addition salts with inorganic acids, e.g. nitric, hydrochloric, hydrobromic, sulphuric, perchloric, and phosphoric acid, or organic acids, e.g. acetic, propionic, glycolic, lactic, oxalic, malonic, malic, tartaric, citric, benzoic, cinnamic, mandelic, methanesulfonic and salicylic acids.

The alkyl, alkylamino, alkylthio and alkoxy groups may be branched or straight chain groups. When $R_5$ and $R_6$ are both alkyl groups, the alkyl group for $R_5$ may be same as or different from the alkyl group for $R_6$.

A halogen atom is preferably fluorine, chlorine or bromine, in particular fluorine or chlorine.

A $C_1$-$C_8$ alkyl group is preferably a $C_1$-$C_6$ alkyl group. A $C_1$-$C_6$ alkyl group is preferably a $C_1$-$C_4$ alkyl group. A $C_1$-$C_4$ alkyl group is e.g. methyl, ethyl, propyl, isopropyl, butyl or tert.butyl, preferably it is methyl or ethyl. A $C_1$-$C_6$ alkoxy group is e.g. methoxy, ethoxy, propoxy, isopropoxy, butoxy or tert.butoxy, preferably it is methoxy or ethoxy. A $C_3$-$C_8$ cycloalkyl group is preferably a cyclopentyl, cyclohexyl or cycloheptyl group. A $C_3$-$C_6$ cycloalkyl ring is preferably a cyclopropyl or cyclopentyl ring.

A thienyl ring is for instance a 2- or 3-thienyl ring. A pyridyl ring is for instance a 2-, 3- or 4, in particular a 3-pyridyl ring. A furyl ring is for instance a 2- or 3-furyl ring.

A substituted phenyl ring is preferably substituted by one or two substituents chosen independently from halogen, $C_1$-$C_4$ alkyl and trifluoromethyl.

When in a —$(CH_2)_m$— or —$(CH_2)_p$—X—$(CH_2)_q$— group, m, p and/or q is greater than 1, then such group may be a branched or straight alkylene chain. A —$(CH_2)_m$— group is for instance a —$CH(R_{14})$— group in which $R_{14}$ is hydrogen or $C_1$-$C_3$ alkyl, or it is a —$CH_2CH_2$— or —$CH_2CH_2CH_2$— group.

A $C_1$-$C_4$ alkyl group substituted by hydroxy is preferably a hydroxymethyl or 1-hydroxyethyl group. A $C_1$-$C_4$ alkyl group substituted by a phenyl ring is preferably a benzyl or phenethyl group, and m is preferably 1 or 2. Each of p and q, being an integer of 1 to 4, it is preferably 1 or 2.

Preferred compounds of the invention are the compounds of formula (I), wherein R is a phenyl ring unsubstituted or substituted by one or two substituents independently chosen from halogen, $C_1$-$C_4$ alkyl and trifluoromethyl; A is a —$(CH_2)_m$— or —$(CH_2)_p$—X—$(CH_2)_q$— group, wherein m is 1 or 2, one of p and q is zero and the other is zero, 1 or 2, and X is —O—, —S— or —NH—; n is zero or 1; each of $R_1$ and $R_2$, independently, is hydrogen or $C_1$-$C_4$ alkyl; $R_3$ is hydrogen or $C_1$-$C_4$ alkyl optionally substituted by hydroxy; $R_3'$ is hydrogen; each of $R_5$ and $R_6$ is independently hydrogen or $C_1$-$C_4$ alkyl; and the pharmaceutically acceptable salts thereof.

More preferred compounds of the invention are the compounds of formula (I), wherein R is phenyl ring unsubstituted or substituted by halogen; A is a —$(CH_2)_m$— or —$(CH_2)_p$—X—$(CH_2)_q$— group, wherein m is 1 or 2; one of p and q is zero and the other is zero or 1 and X is —O—, —S— or —NH—; n is zero; $R_1$ is hydrogen; $R_2$ is hydrogen or $C_1$-$C_4$ alkyl; $R_3$ is hydrogen or $C_1$-$C_2$ alkyl optionally substituted by hydroxy; $R_3'$ is hydrogen; each of $R_5$ and $R_6$ independently is hydrogen or $C_1$-$C_4$ alkyl; and the pharmaceutically acceptable salts thereof.

Examples of particularly preferred compounds of the invention include the following: (S)-2-(4-Benzyloxy-benzylamino)-propionamide; 2-[4-(3-Chloro-benzyloxy)-phenethyl]-amino-acetamide; 2-{[4-(3-Chloro-benzyloxy)-benzyl]methylamino}-acetamide; 2-(4-(3-Chloro-benzyloxy)-benzylamino)-acetamide; (S)-(+)-2-[4-(2-Fluoro-benzyloxy)-benzylamino]-propanamide; (S)-(+)-2-[4-(4-Fluoro-benzyloxy)-benzylamino]-propanamide; (S)-(+)-2-[4-(3-Chloro-benzyloxy)-benzylamino]-propanamide; (R)-(−)-2-[4-(3-Chloro-benzyloxy)-benzylamino]-3-hydroxy-propanamide; (S)-(+)-2-{4-[2-(3-Fluorophenyl)-ethyl]-oxybenzyl}-amino-propanamide; 2-[4-(3-Fluoro-benzyloxy)-benzylamino]-2-methyl-propanamide; and 2-[4-(3-Bromo-benzyloxy)-benzylamino]-2-methyl-propanamide.

These compounds and their salts are referred to herein as "safinamide derivatives".

For convenience, certain terms used in the specification, examples, and appended claims are collected here.

"MAO-B inhibitors" include molecules capable of acting as inhibitors of MAO-B, and pharmaceutically acceptable salts and esters thereof. Members of the MAO-B inhibitor family include both naturally occurring and synthetic molecules. MAO-B inhibitors can be e.g., selegiline, rasagiline, lazabemide or caroxazone. Safinamide can also be considered a potent and selective (reversible) MAO-B inhibitor, but one which possesses additional mechanisms of action such as dopamine re-uptake inhibition and sodium and calcium channel blockade.

A "specific MAO-B inhibitor" or "selective MAO-B inhibitor" is one which inhibits MAO-B more strongly than it inhibits MAO-A. A selective MAO-B inhibitor should inhibit MAO-B at least 10 times more strongly than it inhibits MAO-A. Preferably, the selective MAO-B inhibitor inhibits MAO-B, 100, 1000, 2500, 5000, or 10,000 times more strongly than it inhibits MAO-A.

An "derivative" of a particular compound is one that differs structurally from that original (parent) compound by five or fewer substitutions, or by modification of five or fewer chemical bonds, while retaining the desired activity of the parent compound. Thus, "safinamide derivatives" include molecules whose structures differ from that of safinamide by 5 or fewer substitutions or by modification of five or fewer chemical bonds.

"Combination therapy" (or "co-therapy") includes the administration of safinamide or MAO-B inhibitor and at least a Parkinson's Disease agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). An example of combination therapy for treating Parkinson's Disease with nicotinamide adenine dinucleotide and another PD agent is disclosed in U.S. Pat. No. 4,970,200, specifically incorporated herein by reference.

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally.

Alternatively, for example, all therapeutic agents may be administered orally or all therapeutic agents may be administered by intravenous injection. The sequence in which the therapeutic agents are administered is not narrowly critical. "Combination therapy" also embraces the administration of the therapeutic agents as described above in further combination with other biologically active ingredients and non-drug therapies (e.g., surgery). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks. A combination therapy for PD may include levodopa/PDI (with or without amantidine, COMT inhibitors and/or dopamine agonists) and safinamide (or a safinamide derivative). Alternatively, or in addition, combination therapy for PD may include levodopa/PDI (with or without amantidine, COMT inhibitors and/or dopamine agonists) and a MAO-B inhibitor.

"Parkinson's Disease agents" include levodopa/PDIs such as levodopa plus carbidopa (SINEMET®), levodopa plus controlled release carbidopa (SINEMET-CR®), levodopa plus benserazide (MADOPAR®), levodopa plus controlled release benserazide (MADOPAR-HBS); COMT (catechol-O-methyltransferase) inhibitors such as tolcapone and entacapone; dopamine agonists, such as bromocriptine, pergolide, ropinirole, pramipexole, lisuride, cabergoline, apomorphine, sumanirole, rotigotine, talipexole and dihydroergocriptine; and adamantidine.

Combination therapy includes the administration of safinamide (or a safinamide derivative) or MAO-B inhibitor and one or more dopamine agonists and/or levodopa/PDIs, with or without COMT inhibitors and amantidine. One combination therapy of the invention includes safinamide (or a safinamide derivative) or MAO-B inhibitor and levodopa/PDI. Another combination therapy of the invention includes safinamide or MAO-B inhibitor, levodopa/PDI, and a COMT inhibitor. Another combination therapy of the invention includes safinamide (or a safinamide derivative) or MAO-B inhibitor, levodopa/PDI and a dopamine agonist. Another combination therapy of the invention includes safinamide (or a safinamide derivative) or MAO-B inhibitor, levodopa/PDI, a COMT inhibitor, and a dopamine agonist. Yet another combination therapy of the invention includes safinamide (or a safinamide derivative) or MAO-B inhibitor, levodopa/PDI, a COMT inhibitor, amantidine and a dopamine agonist.

The present invention provides a more effective method of treatment for Parkinson's Disease, and pharmaceutical compositions for treating PD which may be used in such methods. The methods and pharmaceutical compositions of the invention are used to treat symptoms associated with PD. Further, the methods and pharmaceutical compositions of the invention are used to slow the progression of PD.

"Parkinson's Disease symptoms," includes the commonly observed symptoms of Parkinson's Disease, such as those described in: Sulkava, Adv Neurol, 91:411-413, 2003; Facca and Koller, Adv Neurol, 91:383-396, 2003; Marjama-Lyons and Koller, Geriatrics August; 56(8):24-25, 29-30, and 33-35, 2001; Siderowf, Neurol Clin August; 19(3):565-578, 2001; and Poewe, Curr Opin Neurol Neurosurg June; 6(3): 333-338, 1993.

Some symptoms of PD include bradykinesia, or slowness in voluntary movement, which produces difficulty initiating movement as well as difficulty completing movement once it is in progress. The delayed transmission of signals from the brain to the skeletal muscles, due to diminished dopamine, produces bradykinesia. Other symptoms include tremors in the hands, fingers, forearm, or foot, which tend to occur when the limb is at rest but not when performing tasks. Tremor may occur in the mouth and chin as well. Other symptoms of PD include rigidity, or stiff muscles, which may produce muscle pain and an expressionless, mask-like face. Rigidity tends to increase during movement. Other indications of PD include poor balance, due to the impairment or loss of the reflexes that adjust posture in order to maintain balance. Falls are common in people with Parkinson's.

Parkinsonian gait is the distinctive unsteady walk associated with Parkinson's disease. There is a tendency to lean unnaturally backward or forward, and to develop a stooped, head-down, shoulders-drooped stance. Arm swing is diminished or absent and people with Parkinson's tend to take small shuffling steps (called festination). Someone with Parkinson's may have trouble starting to walk, appear to be falling forward as they walk, freeze in mid-stride, and have difficulty making a turn.

The progressive loss of voluntary and involuntary muscle control produces a number of secondary symptoms associated with Parkinson's. Most patients do not experience all of them, and symptoms vary in intensity from person to person. Some secondary symptoms of Parkinson's disease include: bradyphrenia (slow response to questions); constipation; dementia (loss of intellectual capacity)—late in the disease; dysphagia (difficulty swallowing)—saliva and food that collects in the mouth or back of the throat may cause choking, coughing, or drooling; hyperhidrosis (excessive sweating); hypersalivation (excessive salivation); hypophonia (soft, whispery voice); incontinence (loss of bladder and/or bowel control); micrographia (small, cramped handwriting); and psychosocial symptom such as: anxiety, depression, isolation; and seborrhea (scaling, dry skin on the face and scalp).

To evaluate whether a patient is benefiting from the PD treatment, one would examine the patient's symptoms in a quantitative way. In a successful treatment, the patient status will have improved (i.e., the symptoms will have decreased), or the progression will have been retarded (e.g., the patient's condition will have stabilized). The patient's neurons are also evaluated, and a benefited patient will exhibit neuronal protection from oxidative damage (e.g., by magnetic resonance imaging (MRI) behavior in frequent, serial MRI studies and compare the patient's status measurement before and after treatment), SPECT or PET imaging techniques demonstrating sparing of pre- or postsynaptic dopaminergic terminals.

There are a number of standard rating scales for the quantitation of extra-pyramidal neurological deficits. The most complete and validated scale is the Unified Parkinson's Disease Rating Scale (UPDRS). It is subdivided into 6 sections. Part III corresponds to the outcome of a physical examination of motor function and is based on the old "Columbia Scale".

The symptoms of Parkinson's Disease also include changes in the substantia nigra of the brain.

In an embodiment, the invention relates to methods for treating Parkinson's Disease through the administration of safinamide, a safinamide derivative, or a MAO-B inhibitor in combination with other Parkinson's Disease agents or treatments. The inventors have discovered that when safinamide is used in combination with other types of drugs, an unexpected, synergistic effect is achieved. The improvement of symptoms and possibly the delay of disease progression is more evident in patients treated with the combination of drugs than those treated with a single type of drug alone. The unexpected synergistic effect of treatment with safinamide in combination with other PD agents provides a scientific rationale for the use of these co-therapies as novel PD therapy.

In one embodiment, methods of treating Parkinson's Disease are disclosed, wherein safinamide (or a safinamide derivative) or a MAO-B inhibitor and a Parkinson's Disease agent(s) are administered to a subject having Parkinson's Disease, such that the symptoms of Parkinson's Disease are treated or at least partially alleviated. Safinamide (or a safinamide derivative) or a MAO-B inhibitor and Parkinson's Disease agent may be administered as part of a pharmaceutical composition, or as part of a combination therapy. In another embodiment, a patient is diagnosed, e.g., to determine if treatment is necessary, whereupon a combination therapy in accordance with the invention is administered to treat the patient. The amount of safinamide (or a safinamide derivative) or a MAO-B inhibitor and Parkinson's Disease agent(s) is typically effective to reduce symptoms and to enable an observation of a reduction in symptoms.

The methods of treating Parkinson's Disease disclosed, herein include administration of safinamide (or a safinamide derivative) or a MAO-B inhibitor and a dopamine agonist and/or levodopa/PDI and/or COMT inhibitors, and/or amantidine such that the symptoms of Parkinson's Disease are treated or at least partially alleviated. One combination which can be used in the methods of the invention includes safinamide (or a safinamide derivative) or MAO-B inhibitor and levodopa/PDI. Another combination which can be used in the methods of the invention includes safinamide (or a safinamide derivative) or MAO-B inhibitor, levodopa/PDI, and a COMT inhibitor. Another combination which can be used in the methods of the invention includes safinamide (or a safinamide derivative) MAO-B inhibitor, levodopa/PDI, and a dopamine agonist. Another combination which can be used in the methods of the invention includes safinamide (or a safinamide derivative) or MAO-B inhibitor, levodopa/PDI, a COMT inhibitor, and a dopamine agonist. Yet another combination which can be used in the methods of the invention includes safinamide (or a safinamide derivative) or MAO-B inhibitor, levodopa/PDI, a COMT inhibitor, a dopamine agonist and amantidine.

Administration the treatment according to the methods of the invention is made to a subject having Parkinson's Disease, such that the symptoms of Parkinson's Disease are treated or at least partially alleviated. The safinamide (or a safinamide derivative) or MAO-B inhibitor and PD agent may be administered as part of a pharmaceutical composition, or as part of a combination therapy. In another embodiment, a patient is diagnosed, e.g., to determine if treatment is necessary, whereupon a combination therapy in accordance with the invention is administered to treat the patient. The amount of safinamide (or a safinamide derivative) or MAO-B inhibitor and PD agent(s) is typically effective to reduce symptoms and to enable an observation of a reduction in symptoms.

In one embodiment, methods of treating Parkinson's Disease are disclosed, wherein safinamide (or a safinamide derivative) or a MAO-B inhibitor and a Parkinson's Disease agent are administered to a subject having Parkinson's Disease, such that the progression of Parkinson's Disease is at least partially slowed. The safinamide (or a safinamide derivative) or a MAO-B inhibitor and Parkinson's Disease agent(s) may be administered as part of a pharmaceutical composition, or as part of a combination therapy. The amount of safinamide (or a safinamide derivative) or a MAO-B inhibitor and Parkinson's Disease agent(s) is typically effective to retard the progression of PD or to enable an observation of a stabilization in symptoms.

The methods of treating Parkinson's Disease disclosed, herein include administration of safinamide (or a safinamide derivative) or a MAO-B inhibitor and a dopamine agonist and/or levodopa/PDI and/or COMT inhibitors and/or amantidine to a subject having Parkinson's Disease, such that the progression of Parkinson's Disease is at least partially retarded. The safinamide (or a safinamide derivative) or MAO-B inhibitor and PD agent(s) may be administered as part of a pharmaceutical composition, or as part of a combination therapy. The amount of safinamide (or a safinamide derivative) or MAO-B inhibitor and PD agent(s) is typically effective to retard progression of PD and to enable an observation of a stabilization in symptoms. One combination which can be used in the methods of the invention includes safinamide (or a safinamide derivative) or MAO-B inhibitor and levodopa/PDI. Another combination which can be used in the methods of the invention includes safinamide (or a safinamide derivative) or MAO-B inhibitor, levodopa/

PDI and a COMT inhibitor. Another combination which can be used in the methods of the invention includes safinamide (or a safinamide derivative) or MAO-B inhibitor, levodopa/PDI and a dopamine agonist. Another combination which can be used in the methods of the invention includes safinamide (or a safinamide derivative) or MAO-B inhibitor, levodopa/PDI, a COMT inhibitor, and a dopamine agonist. Yet another combination which can be used in the methods of the invention includes safinamide (or a safinamide derivative) or MAO-B inhibitor, levodopa/PDI, a COMT inhibitor, a dopamine agonist and amantidine.

Administration the treatment according to the methods of the invention is made to a subject having Parkinson's Disease, such that the symptoms of Parkinson's Disease are treated or at least partially alleviated. The safinamide (or a safinamide derivative) or MAO-B inhibitor and PD agent(s) may be administered as part of a pharmaceutical composition, or as part of a combination therapy. In another embodiment, a patient is diagnosed, e.g., to determine if treatment is necessary, whereupon a combination therapy in accordance with the invention is administered to treat the patient. The amount of safinamide (or a safinamide derivative) or a MAO-B inhibitor and Parkinson's Disease agent(s) is typically effective to retard the progression of PD or to enable an observation of a stabilization in symptoms.

Safinamide (or a safinamide derivative) may be administered at a dosage of generally between about 1 and about 700 mg/day, advantageously from about 10 to about 300 mg per day, more preferably from about 10 to about 70 or 80 or 150 or 200 or 300 mg/day. For example, safinamide (or a safinamide derivative) may be administered at a dosage of generally between about 0.1 and about 5 mg/kg/day, more preferably from about 0.5 to about 1, 2, 3, 4 or 5 mg/kg/day. Bromocriptine may be administered from 0.5 to 80 mg/day patient: cabergoline from 0.1 to 50 mg/day patient, dihydroergocriptine from 1 to 120 mg/day/patient; lisuride from 0.01 to 20 mg/day patient; pergolide from 0.1 to 20 mg/day/patient; apomorphine from 1 to 200 mg/day/patient; pramipexole from 0.1 to 20 mg/day/patient; ropinirole from 0.1 to 50 mg/day/patient; tolcapone from 10 to 600 mg/day/patient; entacapone from 10 to 600 mg/day/patient; levodopa plus carbidopa (SINEMET®) from 20 to 2000 mg/day/patient and from 10 to 300 mg/day/patient respectively; levodopa plus carbidopa retard (SINEMET-CR®) from 40 to 2400 mg/day and from 10 to 200 mg/day/patient respectively; levodopa plus benserazide (MADOPAR®) from 50 to 1500 mg/day and from 10 to 200 mg/day patient respectively; levodopa plus benserazide retard (MADOPAR-HBS) from 50 to 1500 mg/day and from 10 to 200 mg/day/patient respectively; L-dopa methyl chloridate from 200 to 800 mg; selegiline from 0.1 to 50 mg/day/patient; rasagiline from 0.1 to 10 mg/day/patient, other MAO-B inhibitors may be administered at a dosage of generally between about 0.1 mg/day and about 50 mg/day, more preferably from about 1 mg/day to about 10 mg/day; amantidine from 1 to 2000 mg/day/patient.

As for every drug, the dosage is an important part of the success of the treatment and the health of the patient. The degree of efficacy as a PD treatment depends on the particular drug combination. In every case, in the specified range, the physician has to determine the best dosage for a given patient, according to his sex, age, weight, pathological state and other parameters. Depending on the chosen combination, the amount given to the subject must be appropriate, particularly effective to specifically treat symptoms associated with PD, to slow progression of the disease, to stabilize the observed symptoms, or to produce the desired neuroprotective effects.

Administration may be, e.g., intralesional, intraperitoneal, intramuscular or intravenous injection; infusion; or topical, transdermal, transcutaneous, nasal, oral, ocular or otic delivery. A particularly convenient frequency for the administration of the combination is once a day.

As noted above, combination therapies are part of the invention. The combination therapies of the invention may be administered in any suitable fashion to obtain the desired treatment of PD in the patient. One way in which this may be achieved is to prescribe a regimen of safinamide (or a safinamide derivative) or MAO-B inhibitor so as to "pretreat" the patient to obtain the effects of safinamide (or a safinamide derivative) then follow with the PD agent as part of a specific treatment regimen, e.g., a standard administration of levodopa/PDI (with or without a COMT inhibitor and/or amantidine) and/or a dopamine agonist, to provide the benefit of the co-action of the therapeutic agents.

Combination therapies of the invention include this sequential administration, as well as administration of these therapeutic agents, or at least two of the therapeutic agents, in a substantially simultaneous manner. Substantially simultaneous administration can be accomplished, for example, by administering to the subject a single capsule, pill, or injection having a fixed ratio of safinamide (or a safinamide derivative) and, e.g., a dopamine agonist, or in multiple, single capsules or injections. The components of the combination therapies, as noted above, can be administered by the same route or by different routes. For example, safinamide may be administered by orally, while the other PD agent may be administered intramuscularly or subcutaneously; or all therapeutic agents may be administered orally or all therapeutic agents may be administered by intravenous injection. The sequence in which the therapeutic agents are administered is not believed to be critical.

Administration of the therapies and combination therapies of the invention may be administered (both or individually) orally, topically, subcutaneously, intramuscularly, or intravenously.

The invention further relates to kits for treating patients having PD, comprising a therapeutically effective dose of an agent for treating or at least partially alleviating the symptoms of PD (e.g., levodopa/PDI, a COMT-inhibitor, a dopamine agonist, amantidine and safinamide (or a safinamide derivative) or a MAO-B inhibitor) either in the same or separate packaging, and instructions for its use.

In one aspect, a kit includes therapeutic doses of one or more PD agent(s) and safinamide (or a safinamide derivative) or a MAO-B inhibitor, for treating a patient in need of PD treatment, and instructions for use. In another embodiment, a kit includes therapeutic doses of safinamide (or a safinamide derivative) or MAO-B inhibitor and one or more dopamine agonists for treating a patient in need of PD treatment, and instructions for use. In another embodiment, a kit includes therapeutic doses of safinamide (or a safinamide derivative) or MAO-B inhibitor and one or more levodopa/PDI for treating a patient in need of PD treatment, and instructions for use. In another embodiment, a kit includes therapeutic doses of safinamide (or a safinamide derivative) or MAO-B inhibitor and one or more levodopa/PDI and/or COMT inhibitors for treating a patient in need of PD treatment, and instructions for use. In another embodiment, a kit includes therapeutic doses of safinamide (or a safinamide derivative) or MAO-B inhibitor and one or more levodopa/PDI and/or COMT inhibitors and/or amantidine for treating a patient in need of PD treatment, and instructions for use. In another embodiment, a kit includes therapeutic doses of safinamide (or a safinamide derivative) or MAO-B inhibitor and one or more levodopa/PDI and/or COMT inhibitors and/or amantidine and/or dopamine agonists for treating a patient in need of PD treatment, and instructions for use.

Pharmaceutical compositions comprising safinamide (or a safinamide derivative) or a MAO-B inhibitor and a Parkinson's Disease agent(s), in an effective amount(s) to treat Parkinson's Disease, are also included in the invention.

In one embodiment, a pharmaceutical composition includes therapeutic doses of safinamide (or a safinamide derivative) or MAO-B inhibitor and/or levodopa/PDI and/or dopamine agonists may include additional Parkinson's Disease agents such as COMT inhibitors and/or amantidine for treating a patient in need of PD treatment. One combination which can be used in the pharmaceutical compositions of the invention includes therapeutic doses of safinamide (or a safinamide derivative) or MAO-B inhibitor and levodopa/PDI for treating a patient in need of PD treatment. Another combination which can be used in the pharmaceutical compositions of the invention includes therapeutic doses of safinamide (or a safinamide derivative) or MAO-B inhibitor, levodopa/PDI, and a COMT inhibitor for treating a patient in need of PD treatment. Another combination which can be used in the pharmaceutical compositions of the invention includes therapeutic doses of safinamide (or a safinamide derivative) or MAO-B inhibitor, levodopa/PDI, and a dopamine agonist for treating a patient in need of PD treatment. Another combination which can be used in the pharmaceutical compositions of the invention includes therapeutic doses of safinamide (or a safinamide derivative) or MAO-B inhibitor, levodopa/PDI, a COMT inhibitor and a dopamine agonist for treating a patient in need of PD treatment. Yet another combination which can be used in the pharmaceutical compositions of the invention includes therapeutic doses of safinamide (or a safinamide derivative) or MAO-B inhibitor, levodopa/PDI, a COMT inhibitor, a dopamine agonist, and amantidine for treating a patient in need of PD treatment.

Preferably, treatment should continue as long as Parkinson's Disease symptoms are suspected or observed.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; liposome formulations; or in any other form currently used, including suppositories, creams, lotions, mouthwashes, inhalants and the like.

The compositions and combination therapies of the invention may be administered in combination with a variety of pharmaceutical excipients, including stabilizing agents, carriers and/or encapsulation formulations as described herein. Compositions of the invention may be administered to a PD patient as pharmaceutically acceptable salts and/or in a pharmaceutically acceptable carrier. "Pharmaceutically" or "pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like.

The subject treated by the methods described herein is a mammal, more preferably a human. The following properties or applications of these methods will essentially be described for humans although they may also be applied to non-human mammals, e.g., apes, monkeys, dogs, mice, etc. For human administration, preparations should meet sterility, pyrogenicity, general safety and purity standards as required by FDA Office of Biologics standards.

Pharmaceutically acceptable carriers include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Pharmaceutically acceptable salts include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

In certain embodiments, active compounds may be administered orally. Such compounds are contemplated to include chemically designed or modified agents and liposomal formulations in time release capsules to avoid degradation.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, *acacia*, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

The compositions and combination therapies of the invention can be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Additional formulations suitable for other modes of administration include suppositories. For suppositories, traditional binders and carriers may include, for example, polyallcylene glycols or triglycerides; such suppositories may be formed from mixtures containing the active ingredient in the range of 0.5% to 10%, preferably 1%-2%.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

The pharmaceutical compositions of the present invention can be formulated for oral administration, inhalation devices, depot, intra-adipose, intravenously, sublingually, perilingually, subcutaneously, rectally, or transdermally, or by any other medically-acceptable means, but preferably orally by mixing each of the above compounds with a pharmacologically acceptable carrier or excipient. The amount of active ingredients) that may be combined with desired carrier material(s) to produce single or multiple dosage forms will vary depending upon the host in need thereof and the respective mode of administration. For example, a formulation intended for oral administration of humans may contain from 0.01 mg to 500 mg of active agent(s) compounded with an appropriate convenient amount of carrier material which may vary in composition from about 1 to 99 percent of total composition. Before orally administered drugs enter the general circulation of the human body, they are absorbed into the capillaries of the upper gastrointestinal tract and are transported by the portal vein to the liver. The enzymatic activities, the pH found in gastrointestinal fluids or tissues, the concurrent intake of food and consequent agitation may inactivate the drug or cause the drug to dissolve poorly and consequently decrease compliance, increase the risk of side effects and substantially reduce the efficacy of the drug. Varying dosage unit forms of the present invention comprise safinamide (or a safinamide derivative) or a MAO-B inhibitor in combination with a Parkinson's Disease agent as active ingredients and have surprisingly shown an increase in the efficacy and for inhibiting the progression of PD.

The pharmaceutical compositions of the present invention for inhibiting the progression of PD and/or for treating the disease, comprise safinamide (or a safinamide derivative) or a MAO-B inhibitor in combination with a Parkinson's Disease agent as active ingredients in dosage unit form(s). In cases where the biological half-life of safinamide (or a safinamide derivative) or a MAO-B inhibitor is different than that of a Parkinson's Disease agent, it may be advantageous to administer the drugs in separate or admixed compositions and a controlled release composition may be used for the active compound(s) with the shortest biological half-life. Alternatively, a tablet composition may be used that allows for fast release of the compound(s) with the longest duration and delayed release of the compound(s) with the shortest duration of activity. See, e.g., U.S. Pat. No. 6,500,867, herein incorporated by reference.

The dosage unit forms will generally contain between from about 0.1, 0.5, 1.0, 3.0, 5.0, 10.0, 15.0, to about 200 mg/kg/day of safinamide (or a safinamide derivative) or of a MAO-B inhibitor and from about 0.1 mg to 2000 mg of Parkinson's Disease agent.

The pharmaceutical composition for treating or preventing PD of the present invention can be provided, for example, in the alternative forms prepared by the following procedures:

(1) the above compounds are mixed optionally with a pharmaceutically acceptable excipient or the like by procedures known in the art to provide one dosage form, (2) the respective compounds are independently processed, optionally together with a pharmaceutically acceptable excipient or the like, to use in combination with independent dosage forms, or (3) the respective compounds are independently processed, optionally together with a pharmaceutically acceptable excipient or the like, to provide independently prepared dosage forms as a set.

If the respective compounds are independently processed to provide independently prepared dosage forms, each compound of the pharmaceutical composition of the present invention may be administered to one patient or a prospective patent concurrently or consecutively, and the quantity and period of dosing of the respective compounds need not be the same.

The pharmaceutical composition of the present invention for treating and/or preventing PD can be provided in any and all dosage forms that can be administered to patients by the oral route, such as tablets, fine granules, capsules, and granules, and others. Preferred forms are tablets.

The pharmaceutical composition of the present invention may be manufactured using an excipient, binder, disintegrator, lubricant, and/or other formulation additives. The composition may be provided in sustained release dosage forms. The dosage forms may be manufactured by coating the tablets, granules, fine granules, capsules, etc. with oleaginous substances including, but not limited to, triglycerides, polyglycerol fatty acid esters and hydroxypropylcellulose.

EXAMPLES

Safinamide

Pre-clinical studies of safinamide, including general and specific pharmacology studies on the mechanism of action, toxicology, pharmacokinetics and metabolism, proved that safinamide has a broad spectrum of anticonvulsant activity, with a potency comparable or superior to most classical antiepileptic drugs, without evidence of proconvulsant effect and with a very large safety index (Chazot, Current Opinion in Invest. Drugs, 2(6): 809-813, 2001).

In rodents, administration of safinamide prevented neostriatal dopamine depletion when given prior to the administration of the Parkinson-genic xenobiotic methyl-4-phenyl-1,2,3,6-tetrahydropyridine (MPTP). Moreover, in the same model when given 4 h after the toxin administration, at a time when all the conversion of MPTP to $MPP^+$ (1-methyl-4-phenylpyridine) has occurred, safinamide is capable of preventing nigral neuronal death. In an animal model of wearing off, safinamide restores the efficacy and duration of the motor effect in response to L-dopa, which had diminished after 28 days continuous treatment In toxicological studies in primates after 12 week daily administration of safinamide, a significant increase of neostriatal dopamine with increased turnover was seen (Chazot, Current Opinion in Invest. Drugs, 2(6): 809-813, 2001).

Phase I clinical studies in 71 healthy volunteers revealed that single doses of 10 mg/kg or 7 days of repeated doses of 5 mg/kg/day did not produce any clinically relevant side effect. Overall, the drug was very well tolerated, without objective signs of toxicity and only minor subjective complaints. A tyramine pressure test was performed in 8 healthy volunteers. To raise BP by 30 mm Hg, an equal or greater amount of i.v. tyramine was required after safinamide 2.0 mg/kg compared to placebo, demonstrating lack of "cheese effect," a dangerous hypertensive reaction caused by neural uptake of tyramine from tyramine-containing foods like aged cheeses, certain wines, yeast, beans, chicken liver and herring (Chazot P L, Current Opinion in Invest. Drugs, 2(6): 809-813, 2001).

Safinamide Phase II

A phase II dose finding, double-blind, placebo controlled study to investigate the efficacy and safety of safinamide, a MAO-B inhibitor, in patients affected by idiopathic early Parkinson's disease was performed. The objective of the study was to evaluate the efficacy and safety of orally administered safinamide at two different doses (0.5 mg/kg and 1.0 mg/kg) in parkinsonian patients de-novo or treated with one single dopamine agonist at stable dose. This was a dose finding, double-blind, placebo-controlled, randomized, multicenter, multinational, 12-week trial, comparing two doses of safinamide (0.50 and 1.00 mg/kg) versus placebo as monotherapy or as adjunct therapy to one single dopamine agonist.

Number of patients planned was 150 patients (50 patients per group); number of patients screened was 196 patients; number of patients randomized was: 172 patients; number of patients receiving placebo: 58 patients; number of patients receiving safinamide 0.5 mg/kg: 57 patients; number of patients receiving safinamide 1.0 mg/kg: 57 patients. Analyzed Safety cohort: 168 patients; Placebo: 56 patients; Safinamide 0.5 mg/kg: 56 patients; Safinamide 1.0 mg/kg: 56 patients; ITT cohort: 167 patients; Placebo: 56 patients; Safinamide 0.5 mg/kg: 55 patients; Safinamide 1.0 mg/kg: 56 patients; PP cohort: 156 patients; Placebo: 51 patients; Safinamide 0.5 mg/kg: 54 patients; Safinamide 1.0 mg/kg: 51 patients;

Patients selected were Caucasian male or female outpatients; 30 to 72 years of age; non-smokers; affected by idiopathic Parkinson's disease since at most five years, Hoehn and Yahr stages I-II; de-novo patients responding to L-dopa or apomorphine, defined as patients never treated with any parkinsonian drug or treated with levodopa (+a decarboxylase inhibitor) or one single dopamine agonist for less than four weeks prior to screening visit; patients already treated with one single dopamine agonist at stable doses for at least four weeks prior to the screening visit; written informed consent provided.

Mode of administration was oral, once daily; and duration of treatment was 12 weeks. The primary efficacy variable in this study was the proportion of patients considered to have achieved a response defined as an improvement of at least 30% in the unified Parkinson's disease ratings scale (UPDRS) section III score between baseline (Visit 2) and the end of the study (Visit 9 or early study termination).

Secondary criteria included percentage of patients with an improvement of at least 30% in the UPDRS section III score between baseline (Visit 2) and Visit 5 and Visit 7; changes in the UPDRS sections II and III scores between baseline (Visit 2) and Visit 5, Visit 7 and the end of the study (Visit 9 or early study termination); clinical global impression (CGI) by the investigator during the course of the study; change in Hamilton rating scale for depression (HAMD) between screening (Visit 1) and the end of the study (Visit 9 or early study termination).

Safety was monitored by adverse events, vital signs, 12-lead ECG and clinical laboratory variables.

Statistical Methods:

Intent-to-Treat Cohort

The intent-to-treat (ITT) cohort was defined as all randomized patients who received at least one dose of study medication and for whom at least one UPDRS section III assessment after treatment was available.

The analysis based on the ITT Cohort was considered a primary analysis and was performed for all parameters except safety parameters.

Per-Protocol Cohort

The per-protocol (PP) cohort was defined as all patients who completed the study without major protocol violations. Minor violations not leading to exclusion from the PP cohort were defined during a blind review meeting after data cleaning. Drop-outs due to lack of efficacy and due to adverse events were not excluded from the PP cohort.

The PP analysis was performed for the primary efficacy parameter, demographic data and most important baseline characteristics which were defined in the analysis plan.

Safety Cohort

The safety (S) cohort was defined as all patients who received one dose of study medication and have at least one safety assessment after treatment. Patients were assigned to the study treatment group as randomized.

The analyses based on the safety cohort were performed for the safety parameters, demographic data and the most important baseline characteristics which were defined in the analysis plan.

Demographic data (age, sex, race, etc.), baseline patient characteristics, past medical history and concomitant illnesses were summarized by treatment groups to assess differences between treatment groups and between study cohorts and to characterize the study population as a whole.

The primary efficacy variable was the percentage of patients with an improvement of at least 30% in the UPDRS section III score between baseline (Visit 2) and the end of the study (Visit 9 or early study termination). Comparison between the treatment groups was performed in the ITT analysis cohort (primary analysis) using a logistic regression model taking into account UPDRS section III score at baseline, the patient's treatment history (de-novo, single dopamine agonist alone, single dopamine agonists with a prior Parkinson's disease treatment) and the country. In case of a statistically significant result (p<0.05), additional pairwise comparisons between treatment groups were performed using the same statistical model.

Secondary efficacy variables were the percentage of patients with an improvement of at least 30% in the UPDRS section III score between baseline (Visit 2) and Visit 5 and Visit 7, changes in UPDRS section II and III scores between baseline (Visit 2) and Visit 5, Visit 7 and the end of the study (Visit 9 or early study termination), the CGI during the course of the study and the change in HAMD scores between screening (Visit 1) and the end of the study (Visit 9 or early study termination).

The percentage of patients with an improvement of at least 30% in the UPDRS section III score at Visits 5 and 7 was analyzed using the same methods as for the primary efficacy variable.

Changes in the UPDRS sections II and III scores between baseline (Visit 2) and further visits as well as the change in HAMD score between baseline (Visit 2) and the final visit (Visit 9 or early study termination) were assessed for between-group differences using the Kruskal-Wallis procedure. The normality of the data distribution for the changes in UPDRS and HAMD scores during the study was assessed using the Shapiro-Wilk test.

Treatment differences for the CGI during the conduct of the study were assessed using the Fisher's exact test.

Incidences of adverse events were calculated overall, by body system and by preferred term. Vital sign measurements at baseline (Visit 2) were compared to further visits using the Kruskal-Wallis test. All other safety variables were analysed descriptively.

Efficacy Results:

The percentage of patients with an improvement of at least 30% in the UPDRS section III score between baseline (Visit 2) and the end of the study (Visit 9 or early study termination) and results from the statistical analysis of the primary efficacy variable are displayed in Table 1.

TABLE 1

| | Responder[1] rate at final visit[2] (ITT cohort, N = 167) | | | | | | |
|---|---|---|---|---|---|---|---|
| | Placebo (N = 56) | | Safinamide 0.5 mg/kg (N = 55) | | Safinamide 1.0 mg/kg 2.0 (N = 56) | | Safinamide 0.5 mg/kg versus placebo | Safinamide 1.0 mg/kg 2.0 versus placebo |
| | N | % | N | % | N | % | Overall p-value (logistic regression) |
| Responders[1] | 12 | 21.4 | 17 | 30.9 | 21 | 37.5 | 0.132 | 0.016 |

[1]A responder was defined as a patient with an improvement of at least 30% in UPDRS section III from baseline to the final visit;
[2]Visit 9 or early study termination At the final visit the responder rate was higher in the safinamide groups than in the placebo group. Within the safinamide groups the higher dose resulted in a higher responder rate than in the lower dose.

A statistically significant difference was observed between the safinamide 1.0 mg/kg group and the placebo group for the percentage of patients with an improvement of at least 30% in the UPDRS section III score between baseline (Visit 2) and the final visit (Visit 9 or early study termination). Thus, the superiority of safinamide 1.0 mg/kg to placebo was shown by the analysis of the primary efficacy variable in this study. The observed difference in the primary efficacy variable between safinamide 0.5 mg/kg and placebo was not statistically significant. The results of the PP cohort were consistent with the ITT analysis.

For the secondary efficacy variables, a difference (p=0.049, Fisher's exact test) was seen between the three treatment groups with regard to changes in CGI part I between baseline (Visit 2) and Visit 6 due to the better outcome in the safinamide 0.5 mg/kg group. A first three-subgroup analysis by the patient's treatment history (de-novo, single dopamine agonist alone, and single dopamine agonist and a prior Parkinson's disease treatment) showed that there was no difference in the responder rate, defined as an improvement of at least 30% in the UPDRS section III score between baseline (Visit 2) and the final visit (Visit 9 or early study termination), between the treatment groups within the subgroup of de-novo patients (placebo: 22.7%, 0.5 mg safinamide: 22.7%, 1.0 mg safinamide: 22.7%) at the final visit. Among patients who received a single dopamine agonist alone (placebo: 25.0%, 0.5 mg safinamide: 33.3%, 1.0 mg safinamide: 50.0%) or a dopamine agonist with a prior Parkinson's disease treatment (placebo: 14.3%, 0.5 mg safinamide: 40.0%, 1.0 mg safinamide: 43.8%), the responder rate tended to be higher in the safinamide groups than in the placebo group. In patients treated with a single dopamine agonist the higher safinamide dose resulted in a higher responder rate compared to the lower safinamide dose. At the earlier visits the responder rate tended to be higher in the safinamide groups than in the placebo group. The logistic regression model including all treatment groups did not show a difference in the responder rate between the three treatment groups at the final visit (p≥0.05, logistic regression). However, the study was not powered for this kind of subgroup analysis due to the small number of patients in the study treatment groups in the subgroups. There were no differences between the treatment groups with regard to changes in UPDRS section III scores between baseline (Visit 2) and Visits 5, 7 and the final visit in any of the subgroups (p 0.05, Kruskal-Wallis test).

A further two-subgroup analysis by the patient's treatment history (de-novo versus single dopamine agonist) generally yielded similar results to those of the first subgroup analysis. However, in the second subgroup analysis, the logistic regression model including all treatment groups showed a statistically significant difference between safinamide 1.0 mg/kg and placebo for the responder rates at the final visit in the subgroup of single dopamine agonist patients (p=0.024). There were no relevant differences in the responder rates between safinamide 0.5 mg/kg and placebo in the single dopamine agonist subgroup or between the three treatment groups in the de-novo subgroup. In essence, while in the de novo patients (i.e. patients who were taking either placebo or Safinamide alone) there was no difference in the rate of responders in the 3 study arms; patients under stable dopamine agonist treatment had a rate of responders of 20.6% in the placebo group; of 36.4% in the Safinamide 0.5 mg/kg group and more than double the placebo (47.1%) in the safinamide 1.0 mg/kg.

TABLE 2

| | Placebo (N = 56) | | Safinamide 0.5 mg/kg (N = 55) | | Safinamide 1.0 mg/kg (N = 56) | |
|---|---|---|---|---|---|---|
| | N | % | N | % | N | % |
| De Novo (N = 66) | | | | | | |
| Responders | 5 | 22.7 | 5 | 22.7 | 5 | 22.7 |
| Non Responders | 17 | 77.3 | 17 | 77.3 | 17 | 77.3 |
| Single DA (N = 101) | | | | | | |
| Responders | 7 | 20.6 | 12 | 36.4 | 16 | 47.1 |
| Non Responders | 27 | 79.4 | 21 | 63.6 | 18 | 52.9 |

P = 0.024

Safety Results:

Differences between the treatment groups were seen for the percentage of patients with adverse events, which was higher in the placebo group (50.0% of patients) than in the safinamide 0.5 mg/kg (37.5% of patients) and 1.0 mg/kg (32.1% of patients) groups. Patients most often experienced nervous system disorders in the placebo group (dizziness: 5.4% of patients) and in the safinamide 0.5 mg/kg group (tremor aggravated: 3.6% of patients), whereas in the safinamide 1.0 mg/kg group gastrointestinal system disorders (nausea: 3.6% of patients) were those most frequently reported. Most adverse events were of mild intensity. More related adverse events were reported for the placebo group (25.0% of patients) compared to the safinamide 0.5 mg/kg (12.5% of patients) group and safinamide 1.0 mg/kg (10.7% of patients) group. No deaths were reported in this study. Two patients in the safinamide 0.5 mg/kg group (atrial fibrillation, pregnancy) and one patient in the safinamide 1.0 mg/kg group (myasthenia gravis) experienced serious adverse events.

All of these serious adverse events were assessed as unlikely related (atrial fibrillation) or not related (pregnancy, myasthenia gravis) to the study medication. Two patients were withdrawn due to serious adverse events (atrial fibrillation, myasthenia gravis). A further two patients in the placebo group (abdominal pain, dizziness/confusion) and three patients in the safinamide 0.5 g/kg (hallucination/polynocturia, dizziness, tremor aggravated) withdrew from the study due to non-serious adverse events. Differences were seen between the treatment groups with regard to changes in heart rate between baseline (Visit 2) and Visit 6 (p=0.020) as well as between baseline (Visit 2) and the final visit (p=0.037, Kruskal-Wallis test). In the safinamide 1.0 mg/kg group, mean heart rate increased from baseline to the final visit, while a decrease was observed in the other treatment groups. Overall, no pronounced differences were observed between the treatment groups for other vital signs, ECG recordings and laboratory parameters. Thus, no safety concerns were raised during this study.

In this study, superiority of safinamide 1.0 mg/kg to placebo was demonstrated for the percentage of patients with an improvement of at least 30% in the UPDRS section III score between baseline (Visit 2) and the final visit (Visit 9 or early study termination), the primary efficacy parameter. The improvement in responder rates seen in the overall population appeared to be due to an add-on effect of safinamide in the subgroup of patients treated with a single dopamine agonist. The rate of patients with adverse events was lower in the safinamide groups than in the placebo group. There were no safety concerns associated with the results of laboratory parameters, vital signs and ECG recordings measured during the study.

What is claimed is:

1. A method of treating secondary and psychosocial symptoms of idiopathic Parkinson's disease comprising:
    administering a therapeutically effective stable dose of a single dopamine agonist; and
    concurrently administering a therapeutically effective amount of safinamide, or a pharmaceutically acceptable salt thereof, on an oral daily dosage schedule.

2. The method according to claim 1, wherein said secondary and psychosocial symptoms are selected from bradyphrenia, constipation, dementia, dysphagia, hyperhidrosis, hypersalivation, hypophonia, incontinence, micrographia, anxiety, depression, isolation and seborrhea.

3. The method according to claim 1, wherein safinamide, or a pharmaceutically acceptable salt thereof, is administered for at least 12 weeks.

4. The method according to claim 1, wherein safinamide, or a pharmaceutically acceptable salt thereof, is administered once daily.

5. The method according to claim 1, wherein safinamide is administered as the methanesulfonate salt.

6. The method according to claim 1, wherein the single dopamine agonist is selected from the group consisting of ropinirole, pramiprexole, rotigotine, bromocriptine, cabergoline, lisuride, pergolide, apomorphine, sumanirole, talipexole and dihydroergocriptine.

7. A method of limiting adverse events in a patient with idiopathic Parkinson's disease comprising:
    administering a therapeutically effective stable dose of a single dopamine agonist; and
    concurrently administering a therapeutically effective amount of safinamide, or a pharmaceutically acceptable salt thereof, on an oral daily dosage schedule.

8. The method according to claim 7, wherein safinamide, or a pharmaceutically acceptable salt thereof, is administered for at least 12 weeks.

9. The method according to claim 7, wherein safinamide, or a pharmaceutically acceptable salt thereof, is administered once daily.

10. The method according to claim 7, wherein safinamide is administered as the methanesulfonate salt.

11. The method according to claim 7, wherein the single dopamine agonist is selected from the group consisting of ropinirole, pramiprexole, rotigotine, bromocriptine, cabergoline, lisuride, pergolide, apomorphine, sumanirole, talipexole and dihydroergocriptine.

12. A method of treating idiopathic Parkinson's disease comprising:
    administering a therapeutically effective stable dose of a single dopamine agonist selected from the group consisting of bromocriptine, cabergoline, lisuride, pergolide, apomorphine, sumanirole, talipexole and dihydroergocriptine; and
    concurrently administering a therapeutically effective amount of safinamide, or a pharmaceutically acceptable salt thereof, on an oral daily dosage schedule.

13. The method according to claim 12, wherein safinamide, or a pharmaceutically acceptable salt thereof, is administered for at least 12 weeks.

14. The method according to claim 12, wherein safinamide, or a pharmaceutically acceptable salt thereof, is administered once daily.

15. The method according to claim 12, wherein safinamide is administered as the methanesulfonate salt.

16. The method according to claim 7, wherein the adverse events are selected from abdominal pain, abdominal pain upper, vomiting, diarrhea, somnolence, and headache.

* * * * *